US012605343B2

(12) United States Patent
Hatayama et al.

(10) Patent No.: US 12,605,343 B2
(45) Date of Patent: Apr. 21, 2026

(54) METHOD FOR PRODUCING MICROBUBBLE-CONTAINING ELECTROLYTE SOLUTION AND METHOD FOR PRODUCING MICROBUBBLE-CONTAINING SOLVENT USED FOR PREPARING MICROBUBBLE-CONTAINING ELECTROLYTE SOLUTION

(71) Applicants:Aichi Medical University, Aichi (JP); Sumitomo Seika Chemicals Co., Ltd., Kako-gun (JP)

(72) Inventors: Naoyuki Hatayama, Nagakute (JP); Munekazu Naito, Nagakute (JP); Shuichi Hirai, Nagakute (JP); Kaori Fukushige, Nagakute (JP); Shigeki Sakaue, Kako-gun (JP)

(73) Assignees: Aichi Medical University, Aichi (JP); Sumitomo Seika Chemicals Co., Ltd., Hyogo (JP)

( * ) Notice: Subject to any disclaimer, the term of this patent is extended or adjusted under 35 U.S.C. 154(b) by 427 days.

(21) Appl. No.: 17/773,002

(22) PCT Filed: Aug. 24, 2020

(86) PCT No.: PCT/JP2020/031887
§ 371 (c)(1),
(2) Date: Apr. 28, 2022

(87) PCT Pub. No.: WO2021/084869
PCT Pub. Date: May 6, 2021

(65) Prior Publication Data
US 2022/0387333 A1     Dec. 8, 2022

(30) Foreign Application Priority Data
Oct. 29, 2019     (JP) ................................. 2019-196792

(51) Int. Cl.
*A61K 31/01* (2006.01)
*A61K 9/08* (2006.01)
(Continued)

(52) U.S. Cl.
CPC ............ *A61K 9/5089* (2013.01); *A61K 33/00* (2013.01)

(58) Field of Classification Search
CPC ........ A61K 9/5089; A61K 33/00; A61K 9/08; A61K 31/01; A61K 31/02; A61K 31/336;
(Continued)

(56) References Cited

U.S. PATENT DOCUMENTS 5,565,317 A     10/1996  Dohi et al.
5,686,060 A  *  11/1997  Schneider ............ A61K 49/223
                                                            514/121
(Continued)

FOREIGN PATENT DOCUMENTS

CN        103347493 A      10/2013
CN        109070037 A      12/2018
(Continued)

OTHER PUBLICATIONS

Fiabane et al. (BioMed Research International 2016, Article ID 3572827, 9 pages). (Year: 2016).*
(Continued)

*Primary Examiner* — Ernst V Arnold
(74) *Attorney, Agent, or Firm* — Morgan, Lewis & Bockius LL

(57) ABSTRACT

The present disclosure provides a method for producing an electrolyte solution which can contain a high concentration of micro bubbles, and a method for producing a micro
(Continued)

bubble-containing solvent which can be used for preparing the electrolyte solution, by suppressing decrease in micro bubbles during filtration.

21 Claims, 7 Drawing Sheets

(51) Int. Cl.
$A61K\ 9/50$ (2006.01)
$A61K\ 33/00$ (2006.01)
$A61K\ 47/02$ (2006.01)
$A61P\ 43/00$ (2006.01)

(58) Field of Classification Search
CPC ........ A61K 33/04; A61K 33/06; A61K 33/14; A61K 33/40; A61K 47/02; A01N 1/0226; A61P 43/00; B01D 69/00; B01D 61/14; B01D 61/16
See application file for complete search history.

(56) References Cited

U.S. PATENT DOCUMENTS

| | | | |
|---|---|---|---|
| 2012/0149108 A1 | 6/2012 | Tanabe et al. | |
| 2015/0024010 A1* | 1/2015 | Archambeau ....... B01F 27/2722 | |
| | | | 435/1.2 |
| 2017/0056438 A1* | 3/2017 | Kamei ................. A01N 1/0221 | |
| 2017/0105935 A1 | 4/2017 | Nakashima et al. | |
| 2017/0189943 A1* | 7/2017 | Murata .................. A61K 47/20 | |
| 2019/0029927 A1 | 1/2019 | Takeda et al. | |
| 2019/0298653 A1 | 10/2019 | Yamanouchi et al. | |

FOREIGN PATENT DOCUMENTS

| | | |
|---|---|---|
| JP | H04-149101 A | 5/1992 |
| JP | H06-107538 A | 4/1994 |
| JP | 2006-307053 A | 11/2006 |
| JP | 2010167365 A * | 8/2010 |
| JP | 2012-245086 A | 12/2012 |
| JP | 2014-138925 A | 7/2014 |
| JP | 2014-200762 A | 10/2014 |
| JP | 2016-112031 A | 6/2016 |
| JP | 2016131577 A * | 7/2016 |
| JP | 2016-190646 A | 11/2016 |
| JP | 2017-052739 A | 3/2017 |
| WO | 94/00008 A1 | 1/1994 |
| WO | 2011/021618 A1 | 2/2011 |
| WO | 2012/021860 A1 | 2/2012 |
| WO | 2015/099201 A1 | 7/2015 |
| WO | 2016/084780 A1 | 6/2016 |
| WO | 2017/195852 A1 | 11/2017 |

OTHER PUBLICATIONS

Office Action issued in the corresponding CN Application No. 202080075362.0, dated Apr. 1, 2024.
Extended European Search report issued in corresponding European Patent Application No. 20881071.3 dated Aug. 30, 2023.
Government Public Relations Online, "Join us! Familiar volunteers who can save lives Blood Donation", [online], search on Oct. 29, 2019, Internet <https://www.govonline.go.jp/useful/article/201307/3.html#anc02>.
Japan Organ Transplant Network, "Organ Transplantation", [online], [Search on Oct. 29, 2019], Internet <https://www.jotnw.or.jp/transplant/about.html>.
Office Action issued in corresponding Japanese Patent Application No. 2019-196792 dated Jan. 14, 2020.
International Search Report issued in corresponding International Patent Application No. PCT/JP2020/031887 dated Oct. 20, 2020.
Decision of Rejection issued in corresponding Chinese Patent Application No. 202080075362.0, dated May 28, 2025, with a partial English translation.

\* cited by examiner

Microbubble-containing
physiological saline solution
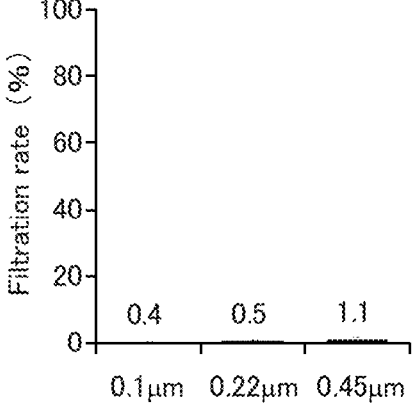
Microbubble-containing solvent to
which no sodium chloride was added
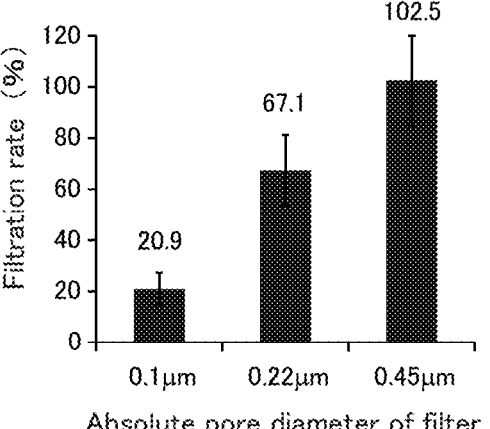
FIG.5A                    FIG.5B

METHOD FOR PRODUCING MICROBUBBLE-CONTAINING ELECTROLYTE SOLUTION AND METHOD FOR PRODUCING MICROBUBBLE-CONTAINING SOLVENT USED FOR PREPARING MICROBUBBLE-CONTAINING ELECTROLYTE SOLUTION

TECHNICAL FIELD

The present invention relates to a method for producing a micro bubble-containing electrolyte solution and a method for producing a micro bubble-containing solvent used for preparing a micro bubble-containing electrolyte solution.

BACKGROUND ART

Platelet formulations are preserved for about 3 days after production from blood as a raw material. Then, if not used during the aforementioned preservation period, the platelet formulations are discarded. As described above, platelet formulations can be preserved only for very short periods of time. Thus, platelet formulations are chronically lacking. Approximately 80% of people receiving blood transfusions are elderly, and it is considered that the number of people receiving blood transfusions will increase in the future due to the aging of the population. On the other hand, in Japan, blood donors decrease, and it is predicted that platelet formulations obtained from blood of about 1 million blood donors will be insufficient in 2027 (Non Patent Literature 1). Therefore, a method for preserving a cell such as a platelet is required.

Organ transplantation is performed to treat patients with impaired or failing functions of organs. However, since donors of organs for organ transplantation are mainly brain dead, the number of organs is insufficient (Non Patent Literature 2). For this reason, it has been attempted to use a cadaveric body as a supply source of an organ, to preserve the organ obtained from the cadaveric body, and then to transplant the organ.

However, since organs obtained from cadaveric bodies are different in periods of time after death to obtain organs, there is a problem that damages to the organs tend to occur during reperfusion after transplantation, and the quality of the organs after preservation is not constant.

CITATION LIST

Non Patent Literature

Non Patent Literature 1: Government Public Relations Online, "Join us! Familiar volunteers who can save lives "Blood Donation", [online], search on Oct. 29, 2019, Internet <gov-online.go.jp/useful/article/201307/3.html#anc02>
Non Patent Literature 2: Japan Organ Transplant Network, "Organ Transplantation", [online], [Search on Oct. 29, 2019], Internet <jotnw.or.jp/transplant/about.html>

SUMMARY OF INVENTION

Technical Problem

Hence, the inventors of the present invention have studied a liquid composition which can be suitably used as a preservation solution and a culture solution of a cell, and a preservation solution of a biological sample such as a tissue, an organ, and the like, and have found that a liquid composition that contains micro bubbles and an electrolyte (hereinafter, also referred to as a "micro bubble-containing electrolyte solution") can be suitably used as a preservation solution and a culture solution of a cell and a preservation solution of a biological sample such as a tissue, an organ, and the like. When the micro bubble-containing electrolyte solution is commercialized, it is necessary to sterilize the micro bubble-containing electrolyte solution before distribution. Sterilization of the preservation solution and the culture solution is generally performed by filtration sterilization. Hence, the inventors of the present invention have found that, when the micro bubble-containing electrolyte solution is filtered, the micro bubble density in the obtained filtrate greatly decreases from the micro bubble density in the micro bubble-containing electrolyte solution before filtration, and a problem arises in that a micro bubble-containing electrolyte solution containing a high concentration of micro bubbles sterilized by filtration cannot be obtained.

With the foregoing in mind, it is an object of the present invention to provide a method for producing an electrolyte solution which can contain a high concentration of micro bubbles by suppressing a decrease in micro bubbles during filtration, and a method for producing a micro bubble-containing solvent which can be used for preparing the electrolyte.

Solution to Problem

In order to achieve the above object, the present invention provides a method for producing a micro bubble-containing electrolyte solution (hereinafter, also referred to as the "electrolyte solution production method"), including the steps of: filtrating a micro bubble-containing solvent with a filter medium; and preparing an electrolyte solution from the obtained filtrate, wherein a cation concentration in the micro bubble-containing solvent is less than 20 mmol/l, and the method satisfies at least one of the following conditions (1), (2) and (3):

Condition (1):
   a micro bubble density in the micro bubble-containing solvent is $1 \times 10^6$ bubbles/ml or more;
Condition (2):
   the method includes the step of preparing the micro bubble-containing solvent by introducing micro bubbles into a solvent; and
Condition (3):
   a micro bubble density in the electrolyte solution is $1 \times 10^5$ bubbles/ml or more.

The present invention also provides a method for producing a micro bubble-containing solvent used for preparing a micro bubble-containing electrolyte solution (hereinafter, also referred to as the "first solvent production method"), including the step of: filtrating a micro bubble-containing solvent with a filter medium, wherein a cation concentration in the micro bubble-containing solvent is less than 20 mmol/l, and the method satisfies at least one of the following conditions (4), (5) and (6):

Condition (4):
   a micro bubble density in the micro bubble-containing solvent is $1 \times 10^6$ bubbles/ml or more;
Condition (5):
   the method includes the step of preparing a micro bubble-containing solvent by introducing micro bubbles into a solvent; and Condition (6):

a micro bubble density in a filtrate is $1 \times 10^5$ bubbles/ml or more.

Advantageous Effects of Invention

According to the present invention, since a decrease in micro bubbles during filtration can be suppressed, a decrease in micro bubble density in the obtained filtrate can be suppressed as compared with a case where the micro bubble-containing electrolyte solution is filtered. Therefore, according to the present invention, it is possible to provide a method for producing an electrolyte solution which can contain a high concentration of micro bubbles, and a method for producing a micro bubble-containing solvent which can be used for preparing the electrolyte solution.

BRIEF DESCRIPTION OF DRAWINGS

FIGS. 5A and 5B are graphs showing the filtration rate in a micro bubble-containing physiological saline solution in Example 3 and in a micro bubble-containing solvent to which no sodium chloride is added.

DESCRIPTION OF EMBODIMENTS

Figure 1:
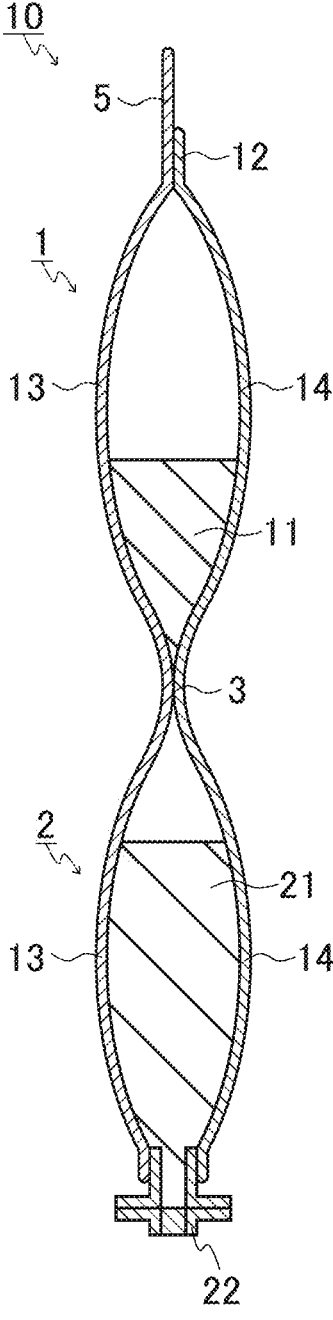
FIG. 1 is a cross sectional view showing an example of a double-chamber container in which an electrolyte solution obtained by the electrolyte solution production method of the present invention and another component are stored.

The present invention also provides a method for producing a micro bubble-containing solvent used for preparing a micro bubble-containing electrolyte solution (hereinafter, also referred to as the "first solvent production method"), including the step of: filtrating a micro bubble-containing solvent with a filter medium, wherein a cation concentration in the micro bubble-containing solvent is less than 20 mmol/l, and the method satisfies at least one of the following conditions (4), (5) and (6):

Condition (4):

a micro bubble density in the micro bubble-containing solvent is $1 \times 10^6$ bubbles/ml or more;

Condition (5):

the method includes the step of preparing the micro bubble-containing solvent by introducing micro bubbles into a solvent; and Condition (6):

a micro bubble density in the filtrate is $1 \times 10^5$ bubbles/ml or more.

\<Electrolyte Solution Production Method\>

As described above, the method for producing a micro bubble-containing electrolyte solution of the present invention includes the steps of: filtrating a micro bubble-containing solvent with a filter medium; and preparing an electrolyte solution from the obtained filtrate, wherein a cation concentration in the micro bubble-containing solvent is less than 20 mmol/l, and the method satisfies at least one of the following conditions (1), (2) and (3):

Condition (1):

a micro bubble density in the micro bubble-containing solvent is $1 \times 10^6$ bubbles/ml or more;

Condition (2):

the method includes the step of preparing the micro bubble-containing solvent by introducing micro bubbles into a solvent; and Condition (3):

a micro bubble density in the electrolyte solution is $1 \times 10^5$ bubbles/ml or more.

The electrolyte solution production method of the present invention is characterized in that a cation concentration in a micro bubble-containing solvent to be subjected to the filtrating is set to less than 20 mmol/l, and other steps and conditions are not particularly limited.

As a result of intensive studies, the inventors of the present invention have found that cations in a micro bubble-containing electrolyte solution, particularly monovalent cations, are associated with a decrease in micro bubbles during filtration. Further, the inventors of the present invention have found that, by setting the cation concentration in the micro bubble-containing solvent to be subjected to filtration less than the aforementioned concentration, the decrease in micro bubbles during filtration can be suppressed, thereby made the present invention. Therefore, according to the present invention, since the decrease in micro bubbles during filtration can be suppressed, the decrease in micro bubble density in the obtained filtrate can be suppressed as compared with a case where the micro bubble-containing electrolyte solution is filtered. Accordingly, according to the present invention, it is possible to produce an electrolyte solution which can contain a high concentration of micro bubbles.

In the present invention, "micro bubble" means a closed minute space made of a gas surrounded by something other than the gas, and can also be referred to as, for example, a minute bubble. The micro bubble may be, for example, a fine bubble. The fine bubble generally means a micro bubble having a bubble diameter of less than 100 µm. The bubble diameter means a spherical equivalent diameter of the bubble. The bubble diameter may be a mean diameter (arithmetic mean diameter) of micro bubbles obtained by the measurement method to be described below. The fine bubble may be a microbubble or an ultrafine bubble. The microbubble generally means a micro bubble having a bubble diameter of 1 µm or more and less than 100 µm. The ultrafine bubble generally means a micro bubble having a bubble diameter of less than 1 µm.

In the present invention, the micro bubbles are present dispersed in a solvent. The micro bubbles are present dispersed in whole or in part in the solvent. In the latter case, it can be also said that the micro bubbles are localized to a part of the solvent. The solvent can be, for example, a liquid or a solid. Examples of the liquid include aqueous solvents including water, oily solvents, and mixed solvents thereof. The liquid also includes a sol. Examples of the solid include solids obtained by coagulating the liquid. The solid also includes a gel.

The density, bubble diameter, and mean diameter of the micro bubbles (hereinafter also referred to as "characteristics") can be appropriately measured according to the medium in which the micro bubbles are dispersed. When the micro bubbles are dispersed in a liquid solvent, the characteristics of the micro bubbles can be calculated by analyzing the bubbles in the solvent by a particle tracking analysis method. The particle tracking analysis method can be performed, for example, using NanoSight® NS300 (produced by Malvern Instrument) according to Example 1 to be described below. The characteristics of the micro bubbles may be calculated by an analysis method other than the particle tracking analysis method. In that case, the characteristics of the micro bubbles obtained by the other analysis method satisfy the example condition of the present embodiment when converted into the calculated value obtained by the particle tracking analysis method. When the micro bubbles are dispersed in a solid solvent, the characteristics of the micro bubbles can be calculated based on the characteristics of the micro bubbles in the liquid before solidification of the medium and the characteristics of the micro bubbles in the liquid obtained by dissolving the solid medium.

In the present invention, a "high concentration of micro bubbles" means a high micro bubble density in a solvent as compared with a solvent (e.g., water, pure water, or the like) in which no micro bubbles are introduced. Specifically, the "high concentration of micro bubbles" means, for example, that the micro bubble density in a solvent is $1 \times 10^6$ bubbles/ml, $5 \times 10^6$ bubbles/ml, $1 \times 10^7$ bubbles/ml, $5 \times 10^7$ bubbles/ml, or $1 \times 10^8$ bubbles/ml or more.

In the present invention, an "electrolyte" means a substance which ionizes into a cation and an anion when dissolved in a solvent. Examples of the electrolyte include the electrolytes added to a physiological saline solution, an extracellular fluid, an intracellular fluid, an infusion, a culture solution, a preservation solution, a perfusate, a dialysate, and a drug solution. Specific examples of the electrolyte include chloride such as sodium chloride, potassium chloride, calcium chloride, magnesium chloride, ferric chloride or its hydrate, and manganese chloride or its hydrate; carbonate such as sodium carbonate and sodium bicarbonate; phosphates such as disodium phosphate, disodium hydrogen phosphate, sodium dihydrogen phosphate, and potassium dihydrogen phosphate; sulfates such as copper sulfate or its hydrate, magnesium sulfate, and sodium sulfate ester; sulfite such as sodium bisulfite; iodide such as potassium iodide; lactate such as sodium L-lactate; acetate such as chondroitin potassium acetate; and citrate such as sodium citrate, and the like.

The electrolyte is, for example, an electrolyte which, when dissolved in a solvent, ionizes sodium ions ($Na^+$), potassium ions ($K^+$), magnesium ions ($Mg^{2+}$), calcium ions ($Ca^{2+}$), manganese ions ($Mn^{2+}$), zinc ions ($Zn^{2+}$), copper ions ($Cu^{2+}$), iron ions (divalent) ($Fe^{2+}$), iron ions (trivalent) ($Fe^{3+}$), chloride ions ($Cl^-$), iodide ions ($I^-$), hydrogen carbonate ions ($HCO_3^-$), carbonate ions ($CO_3^{2-}$), phosphate ions ($PO_4^{2-}$), hydrogen phosphate ions ($HPO_4^-$), sulfate ions ($SO_4^2$), acetate ions ($CH_3COO^-$), L-lactate ions ($CH_3CH(OH)COO^-$), citrate ions ($C(OH)(CH_2COOH)_2 COO^-$), and the like.

In the present invention, an "electrolyte solution" means a composition in which the electrolyte is dispersed in a solvent. It is preferable that a part or the whole of the electrolyte is dissolved in a solvent. The solvent may be, for example, an aqueous solvent including water, and is preferably water, distilled water, or pure water. The aqueous solvent may include a non-aqueous solvent such as alcohol.

Examples of the electrolyte solution include infusions including extracellular fluids such as a physiological saline solution, a Ringer's solution, a lactated Ringer's solution, an acetated Ringer's solution, and a bicarbonate Ringer's solution (isotonic electrolyte infusion or extracellular fluid supplement), intracellular fluids such as a starting solution, a dehydrated supplement, a maintenance solution, and a postoperative recovery solution (hypotonic electrolyte infusion or intracellular fluid supplement), enteral nutrition, and enema; preservation solutions including organ preservation solutions such as a University of Wisconsin (UW) solution, a histidine-tryptophan-ketoglutarate (HTK) solution, a Celsoir solution, an ET-Kyoto solution, an IGL-1 solution, Polysol solution, and an Euro-Collins solution, and cell preservation solutions; culture solutions including cell culture solutions such as a MEM medium, a DMEM medium, and a RPMI1640 medium, and bacterial culture solutions; perfusates such as an organ perfusate, a dialysis perfusate, and a surgical perfusate; dialysates such as a peritoneal dialysis solution; and drug solutions such as a nebulizer drug solution, an injection, an oral solution, an eye drop, a nasal administration drug, and a vaginal administration drug, and the like.

In the electrolyte solution production method of the present invention, a micro bubble-containing solvent is subjected to filtration in the filtrating. Thus, the electrolyte solution production method of the present invention may include the step of preparing a micro bubble-containing solvent by introducing micro bubbles into a solvent. In other words, the electrolyte solution production method of the present invention may satisfy the above condition (2).

The solvent-preparing can be carried out by a method of producing a micro bubble such as fine bubble using a freely selected gas. As a specific example, when the composition of the present invention is a liquid, the micro bubble-containing solvent can be produced by using, for example, a freely selected gas, the solvent, and a micro bubble production apparatus of a swirling flow type, an ejector type, a venturi type, a static mixer type, a micro-pore type, a pressure melting type, or an ultrasonic cavitation type. At the start of the solvent-preparing, the freely selected gas is in a state of a gas, a liquid, or a solid. The freely selected gas is composed of one or more types of gases. When the freely selected gas is composed of a plurality of types of gases, in the solvent-preparing, each gas may be separately introduced into the solvent, or all or some of the freely selected gases may be simultaneously introduced into the solvent.

The type of the freely selected gas is not particularly limited, and may be appropriately determined according to, for example, the type of the electrolyte solution. Examples of the freely selected gas include biogas such as carbon monoxide (CO), nitrogen monoxide (NO), hydrogen sulfide ($H_2S$), and hydrogen ($H_2$); rare gas such as helium (He), argon (Ar), krypton (Kr), and xenon (Xe); carbon dioxide ($CO_2$); nitrous oxide ($N_2O$); nitrogen dioxide ($NO_2$); nitrogen ($N_2$); oxygen ($O_2$); ozone ($O_3$), methane ($CH_4$); ethane ($CH_3CH_3$); propane ($CH_3CH_2CH_3$); fluoromethane ($CH_3F$); difluoromethane ($CH_2F_2$); carbon tetrafluoride ($CF_4$), ethylene oxide ($C_2H_4O$); and air. In the present application, the "biological gas" means a gas containing carbon monoxide (CO), nitric oxide (NO), hydrogen sulfide ($H_2S$), or hydrogen ($H_2$), or a mixed gas containing two or more of these. In the present invention, the "air" means, for example, air (atmosphere) used in producing the micro bubbles. It is preferable that the gas in the micro bubbles is a gas derived from a medical gas when it has a medical gas grade.

The micro bubble density in the micro bubble-containing solvent obtained in the solvent-preparing is not particularly limited, and is increased as compared with the micro bubble density in the solvent before the solvent-preparing. Further, the micro bubble density in the micro bubble-containing solvent obtained in the solvent-preparing may be set according to, for example, the degree of a decrease in micro bubbles in the filtrating and a desired micro bubble density in the electrolyte solution. In the present invention, the "micro bubble density" means the number of micro bubbles relative to the volume of the solvent. The "density" can also be referred to as a number concentration.

The micro bubble density in the micro bubble-containing solvent is, for example, $1\times10^6$ bubbles/ml or more. In other words, the micro bubble density in the micro bubble-containing solvent satisfies, for example, the condition (1). The lower limit of the micro bubble density in the micro bubble-containing solvent is preferably $5\times10^6$ bubbles/ml, $1\times10^7$ bubbles/ml, $5\times10^7$ bubbles/ml, $1\times10^8$ bubbles/ml, $5\times10^8$ bubbles/ml, $1\times10^9$ bubbles/ml, and more preferably $1\times10^6$ bubbles/ml, $5\times10^6$ bubbles/ml, $1\times10^7$ bubbles/ml, $5\times10^7$ bubbles/ml, $1\times10^8$ bubbles/ml, or $5\times10^8$ bubbles/ml. The upper limit of the micro bubble density in the micro bubble-containing solvent is, for example, $1.5\times10^9$ bubbles/ml, $2\times10^9$ bubbles/ml, $3\times10^9$ bubbles/ml, $5\times10^9$ bubbles/ml, $7\times10^9$ bubbles/ml, $9\times10^9$ bubbles/ml, $1\times10^{10}$ bubbles/ml, $5\times10^{10}$ bubbles/ml, $1\times10^{11}$ bubbles/ml, $5\times10^{11}$ bubbles/ml, $1\times10^{12}$ bubbles/ml, or $5\times10^{12}$ bubbles/ml. The micro bubble density in the micro bubble-containing solvent is in the range, for example, from $1\times10^6$ bubbles/ml to $1\times10^{12}$ bubbles/ml, from $1\times10^6$ bubbles/ml to $1\times10^{11}$ bubbles/ml, from $1\times10^6$ bubbles/ml to $5\times10^{10}$ bubbles/ml, from $1\times10^6$ bubbles/ml to $1\times10^{10}$ bubbles/ml, from $1\times10^6$ bubbles/ml to $9\times10^9$ bubbles/ml, from $5\times10^6$ bubbles/ml to $9\times10^9$ bubbles/ml, from $1\times10^7$ bubbles/ml to $7\times10^9$ bubbles/ml, from $5\times10^7$ bubbles/ml to $7\times10^9$ bubbles/ml, from $1\times10^8$ bubbles/ml to $5\times10^9$ bubbles/ml, from $5\times10^8$ bubbles/ml to $5\times10^9$ bubbles/ml, from $1\times10^9$ bubbles/ml to $3\times10^9$ bubbles/ml, from $5\times10^8$ bubbles/ml to $2\times10^9$ bubbles/ml, or from $5\times10^8$ bubbles/ml to $1.5\times10^9$ bubbles/ml.

The electrolyte solution production method of the present invention may include the step of adjusting a cation concentration in the micro bubble-containing solvent to less than 20 mmol/l prior to the filtrating if the cation concentration in the micro bubble-containing solvent before or after the solvent-preparing does not satisfy the aforementioned numerical range. Specifically, first, in the concentration-adjusting, the cation concentration in the micro bubble-containing solvent before or after the solvent-preparing is measured. Regarding the method for measuring the cation concentration, reference can be made to the description to be described below. Then, in the concentration-adjusting, when the cation concentration in the micro bubble-containing solvent before or after the solvent-preparing is 20 mmol/l or more, for example, the micro bubble-containing solvent before or after the solvent-preparing is diluted by a solvent (dilution solvent). The dilution solvent may be, for example, the same as or different from the solvent in the micro bubble-containing solvent, and is preferably the same. The dilution solvent is preferably an aqueous solvent, and more preferably water, distilled water, or pure water. The cation concentration in the dilution solvent is less than 20 mmol/l. Regarding the cation concentration in the dilution solvent, for example, reference can be made to the cation concentration in the micro bubble-containing solvent to be described below.

Next, in the filtrating, a micro bubble-containing solvent is filtered with a filter medium. The filtration method in the filtrating may be appropriately determined according to the type of the filter medium, and examples thereof include natural filtration, vacuum filtration, pressure filtration, and centrifugal filtration.

In the filtrating, the cation concentration in the micro bubble-containing solvent is less than 20 mmol/l. The cation concentration is preferably 17 mmol/l or less, 10 mmol/l or less, more preferably 2, 1.7, or 1 mmol/l or less, and still more preferably 0.2, 0.17, or 0.1 mmol/l or less, for example, because the decrease in micro bubbles during filtration can be suppressed. The cation concentration in the micro bubble-containing solvent is, for example, 0 mmol/l or more, more than 0 mmol/l, or 0.2, 0.17, or 0.1 mmol/l or more. The range of the cation concentration may be, for example, a combination of the above-described ranges.

The cation is, for example, a monovalent cation, and specific examples thereof include cations of alkali metal such as a sodium ion and a potassium ion. The cation is preferably a sodium ion or a potassium ion. One or two or more types of the monovalent cations may be used. In the latter case, the cation concentration is, for example, a total concentration of two or more types of monovalent cations.

When the micro bubble-containing solvent contains a monovalent cation, the monovalent cation concentration is, for example, less than 20 mmol/l, and is preferably 17 mmol/l or less, 10 mmol/l or less, more preferably 2, 1.7, or 1 mmol/l or less, and still more preferably 0.2, 0.17, or 0.1 mmol/l or less, for example, because the decrease in micro bubbles during filtration can be suppressed. The monovalent cation concentration in the micro bubble-containing solvent is, for example, 0 mmol/l or more, more than 0 mmol/l, or 0.2, 0.17, or 0.1 mmol/l or more. The range of the monovalent cation concentration may be, for example, a combination of the above-described ranges.

The cation may include a cation of divalent or more, and examples thereof include a divalent cation and a trivalent cation. Specific examples of the divalent cation include cations of alkaline earth metal such as calcium ion ($Ca^{2+}$) and magnesium ion ($Mg^{2+}$), and is preferably calcium ion or magnesium ion. One or two or more types of the divalent cation may be used. In the latter case, the divalent cation concentration is, for example, a total concentration of two or more divalent cations. The trivalent cation may be, for example, aluminium ion ($Al^{3+}$). One or two or more types of the trivalent cations may be used. In the latter case, the trivalent cation concentration is, for example, a total concentration of two or more types of trivalent cations.

When the micro bubble-containing solvent contains a divalent cation, the divalent cation concentration is, for example, 10 mmol/l or less, and is preferably 1 mmol/l or less, more preferably 0.1 mmol/l or less, and still more preferably 0.01 mmol/l or less, for example, because the decrease in micro bubbles during filtration can be suppressed. The divalent cation concentration in the micro bubble-containing solvent is, for example, 0 mmol/l or more, more than 0 mmol/l, or 0.01 mmol/l or more. The range of the divalent cation concentration may be, for example, a combination of the above-described ranges.

When the micro bubble-containing solvent contains a trivalent cation, the trivalent cation concentration is, for example, less than 0.1 mmol/l, and is preferably 0.01 mmol/l or less, and more preferably 0.001 mmol/l or less, for example, because the decrease in micro bubbles during filtration can be suppressed. The trivalent cation concentration in the micro bubble-containing solvent is, for example, 0 mmol/l or more, more than 0 mmol/l, or 0.001 mmol/l or more. The range of the trivalent cation concentration may be, for example, a combination of the above-described ranges.

The cation concentration in the micro bubble-containing solvent can be measured, for example, by inductively coupled plasma (ICP) emission spectrometric analysis, ICP mass spectrometry analysis, or ion chromatography.

The filter medium is not particularly limited, and is, for example, a filter medium having voids, and is preferably a filter. The type of the filter is not particularly limited, and examples thereof include filter paper, woven fabric, nonwoven fabric, porous body, mesh, membrane and the like. The material of the filter is not particularly limited, and examples thereof include glass, polymer, cellulose and the like. Examples of the filter include a glass filter such as glass fiber filter paper, a polymer filter such as a polymer porous body, and a filter paper such as cellulose and the like. Examples of the polymer include polytetrafluoroethylene (PTFE), polyvinylidene fluoride (PVDF), polyethersulfone (PES), cellulose-mixed esters (MCE) and the like. When the filter medium is a filter, the filter medium may be an integral type filtration device such as a syringe filter. The filter medium is preferably a membrane filter, and more preferably a membrane filter made of a polymer.

In the filtrating, the type and number of the filter media used for the filtration are not particularly limited. As to the type of the filter medium, for example, one type of the filter media may be used alone, or two or more types of them may be used in combination. As to the number of the filter media, for example, one filter medium may be used alone or two or more of them may be used in combination.

The size of the void of the filter medium is not particularly limited. The void may be referred to as, for example, a pore size, a particle retention capacity, an opening, a basis weight, a pore diameter, or the like, depending on the type of the filter medium. The pore diameter is, for example, an average pore diameter or an absolute pore diameter. The absolute pore diameter of the filter medium is not particularly limited, and is, for example, in the range from 10 to 450 nm, in the range from 50 to 450 nm, preferably in the range from 100 to 450 nm, and more preferably in the range from 100 to 200 nm, in the range from 100 to 220 nm, in the range from 200 to 450 nm, or in the range from 220 to 450 nm. The absolute pore diameter is, for example, a pore diameter measured by absolute filtration accuracy, and means that the filtration inhibition rate (particle retention capacity) of particles of a predetermined size is at a predetermined ratio or more. The predetermined ratio is, for example, 90%, 91%, 92%, 93%, 94%, 95%, 96%, 97%, 98%, 99%, 99.5%, or 99.9% or more. As a specific example, when the absolute pore diameter of the filter medium is 200 nm, it can be said that a filtration inhibition rate of particles of 200 nm of the filter medium is at a predetermined ratio or more.

When the absolute pore diameter of the filter medium is in the range from 100 to 450 nm, microorganisms and the like in the micro bubble-containing solvent can be almost removed, and therefore, it can be said that the obtained filtrate is sterilized. Also, in general, sterilization of liquid compositions has been carried out using a filter medium having an absolute pore diameter in the range from 100 to 220 nm. Thus, in the filtrating, when a micro bubble-containing solvent is filtered using a filter medium having an absolute pore diameter in the range from 50 to 450 nm, from 100 to 450 nm, or from 100 to 220 nm, the filtrating may be referred to as a filtration sterilizing.

The micro bubble density in the filtrate obtained in the filtrating is not particularly limited, and, for example, the density is $1 \times 10^5$ bubbles/ml or more (condition (6)). The lower limit of the micro bubble density in the filtrate is preferably $1 \times 10^6$ bubbles/ml, $5 \times 10^6$ bubbles/ml, $1 \times 10^7$ bubbles/ml, $5 \times 10^7$ bubbles/ml, $1 \times 10^8$ bubbles/ml, $5 \times 10^8$ bubbles/ml, or $1 \times 10^9$ bubbles/ml, and preferably $1 \times 10^6$ bubbles/ml, $5 \times 10^6$ bubbles/ml, $1 \times 10^7$ bubbles/ml, $5 \times 10^7$ bubbles/ml, $1 \times 10^8$ bubbles/ml, or $5 \times 10^8$ bubbles/ml, for example, because the electrolyte solution can be suitably used as a low material liquid such as a preservation solution, a culture solution, or an infusion. The upper limit of the micro bubble density in the electrolyte solution is, for example, $1.5 \times 10^9$ bubbles/ml, $2 \times 10^9$ bubbles/ml, $3 \times 10^9$ bubbles/ml, $5 \times 10^9$ bubbles/ml, $7 \times 10^9$ bubbles/ml, $9 \times 10^9$ bubbles/ml, $1 \times 10^{10}$ bubbles/ml, $5 \times 10^{10}$ bubbles/ml, $1 \times 10^{11}$ bubbles/ml, $5 \times 10^{11}$ bubbles/ml, $1 \times 10^{12}$ bubbles/ml, or $5 \times 10^{12}$ bubbles/ml. The micro bubble density in the electrolyte solution is in the range, for example, from $1 \times 10^5$ bubbles/ml to $5 \times 10^{12}$ bubbles/ml, from $5 \times 10^5$ bubbles/ml to $5 \times 10^{12}$ bubbles/ml, from $5 \times 10^5$ bubbles/ml to $1 \times 10^{12}$ bubbles/ml, from $5 \times 10^5$ bubbles/ml to $5 \times 10^{11}$ bubbles/ml, from $5 \times 10^5$ bubbles/ml to $1 \times 10^{11}$ bubbles/ml, from $5 \times 10^5$ bubbles/ml to $5 \times 10^{10}$ bubbles/ml, from $5 \times 10^5$ bubbles/ml to $1 \times 10^{10}$ bubbles/ml, from $1 \times 10^6$ bubbles/ml to $9 \times 10^9$ bubbles/ml, from $5 \times 10^6$ bubbles/ml to $9 \times 10^9$ bubbles/ml, from $1 \times 10^8$ bubbles/ml to $7 \times 10^9$ bubbles/ml, from $5 \times 10^7$ bubbles/ml to $7 \times 10^9$ bubbles/ml, from $1 \times 10^8$ bubbles/ml to $5 \times 10^9$ bubbles/ml, from $5 \times 10^8$ bubbles/ml to $5 \times 10^9$ bubbles/ml, from $1 \times 10^9$ bubbles/ml to $3 \times 10^9$ bubbles/ml, from $5 \times 10^8$ bubbles/ml to $2 \times 10^9$ bubbles/ml, or from $5 \times 10^8$ bubbles/ml to $1.5 \times 10^9$ bubbles/ml.

Next, in the electrolyte solution-preparing, an electrolyte solution is prepared from the obtained filtrate. In the electrolyte solution-preparing, the electrolyte solution can be prepared by adding an electrolyte to the filtrate depending on the type and composition of the electrolyte solution. The electrolyte may be a solid or a liquid. In the latter case, since the electrolyte is diluted by mixing with the filtrate to compose the electrolyte solution, it can be said to be a concentrated solution of an electrolyte solution.

The micro bubble density in the electrolyte solution obtained in the electrolyte solution-preparing is not particularly limited, and, for example, the density is $1 \times 10^5$ bubbles/ml or more. In other words, the micro bubble density in the electrolyte solution satisfies, for example, the condition (3). The lower limit of the micro bubble density in the electrolyte solution is preferably $1 \times 10^6$ bubbles/ml, $5 \times 10^8$ bubbles/ml, $1 \times 10^7$ bubbles/ml, $5 \times 10^7$ bubbles/ml, $1 \times 10^8$ bubbles/ml, $5 \times 10^8$ bubbles/ml, or $1 \times 10^9$ bubbles/ml, and preferably $1 \times 10^6$ bubbles/ml, $5 \times 10^8$ bubbles/ml, $1 \times 10^7$ bubbles/ml, $5 \times 10^7$ bubbles/ml, $1 \times 10^8$ bubbles/ml, or $5 \times 10^8$ bubbles/ml, because the electrolyte solution can be suitably used as a preservation solution, a culture solution, or an infusion. The upper limit of the micro bubble density in the electrolyte solution is, for example, $1.5 \times 10^9$ bubbles/ml, $2 \times 10^9$ bubbles/ml, $3 \times 10^9$ bubbles/ml, $5 \times 10^9$ bubbles/ml, $7 \times 10^9$ bubbles/ml, $9 \times 10^9$ bubbles/ml, $1 \times 10^{10}$ bubbles/ml, $5 \times 10^{10}$ bubbles/ml, $1 \times 10^{11}$ bubbles/ml, $5 \times 10^{11}$ bubbles/ml, $1 \times 10^{12}$ bubbles/ml, or $5 \times 10^{12}$ bubbles/ml. The micro bubble density in the electrolyte solution is in the range, for example, from $1 \times 10^5$ bubbles/ml to $5 \times 10^{12}$ bubbles/ml, from $5 \times 10^5$ bubbles/ml to $5 \times 10^{12}$ bubbles/ml, from $5 \times 10^5$ bubbles/ml to $1 \times 10^{12}$ bubbles/ml, from $5 \times 10^5$ bubbles/ml to $5 \times 10^{11}$ bubbles/ml, from $5 \times 10^5$ bubbles/ml to $1 \times 10^{11}$ bubbles/ml, from $5 \times 10^5$ bubbles/ml to $5 \times 10^{10}$ bubbles/ml, from $5 \times 10^5$ bubbles/ml to $1 \times 10^{10}$ bubbles/ml, from $1 \times 10^6$ bubbles/ml to $9 \times 10^9$ bubbles/ml, from $5 \times 10^6$ bubbles/ml to $9 \times 10^9$ bubbles/ml, from $1 \times 10^7$ bubbles/ml to $7 \times 10^9$ bubbles/ml, from $5 \times 10^7$ bubbles/ml to $7 \times 10^9$ bubbles/ml, from $1 \times 10^8$ bubbles/ml to $5 \times 10^9$ bubbles/ml, from $5 \times 10^8$ bubbles/ml to $5 \times 10^9$ bubbles/ml, from $1 \times 10^9$ bubbles/ml to $3 \times 10^9$ bubbles/ml, from $5 \times 10^8$ bubbles/ml to $2 \times 10^9$ bubbles/ml, or from $5 \times 10^8$ bubbles/ml to $1.5 \times 10^9$ bubbles/ml.

In the electrolyte solution-preparing, for example, other component may be added. Examples of the other component include sugars such as glucose; proteins such as serum albumin and immunoglobulin; drugs such as antimicrobial agents; pH adjusting agents such as citric acid hydrate, sodium hydroxide, and sodium dihydrogen phosphate; stabilizing agents such as chondroitin sulfate sodium and sodium bisulfite vitamins such as thiamine chloride hydrochloride, pyridoxine hydrochloride, cyanocobalamin, panthenol, riboflavin phosphate sodium, nicotinamide, and ascorbic acid; and solubilizing agents such as polysorbate 80 and polysorbate 20.

The electrolyte solution production method of the present invention may satisfy any one or more of the conditions (1) to (3), and satisfies one, two, or three of them. The electrolyte solution production method of the present invention preferably satisfies the condition (3) because, for example, the electrolyte solution can be suitably used as a preservation solution, a culture solution, or an infusion.

In the electrolyte solution production method of the present invention, the electrolyte solution may be filled into a container (the electrolyte solution-filling). Thus, the micro bubble-containing electrolyte solution can be easily transported and stored. The method of filling the container can be appropriately determined according to, for example, the form of the container.

The container includes one or more storage spaces for a liquid, a gas or a solid. If the container includes one or more storage spaces, the electrolyte solution is filled into any one or more of the storage spaces of the container in the electrolyte solution-filling.

Hereinafter, a case where the container includes two storage spaces will be described as an example. In this case, the container includes, for example, a first chamber and a second chamber. Each of the first chamber and the second chamber may be configured independently, that is, may be configured as independent containers, or may be configured integrally, that is, may be configured as a single container. In the former case, the container can also be referred to as a container kit. In the latter case, that is, in the case where the first chamber and the second chamber are configured as a single container, the container preferably includes an isolation portion that can isolate the first chamber and the second chamber. When the container includes an isolation portion, the first chamber and the second chamber are arranged so as to sandwich the isolation portion, for example. When the electrolyte and the other component are mixed to use as the electrolyte solution, the isolation portion is preferably configured to communicate the first chamber and the second chamber.

A double-chamber container for medical use can be used as the container including the first chamber and the second chamber, for example. As the double-chamber container, for example, a plastic double bag in which a plurality of chambers are formed by providing the isolating portion in a plastic bag (e.g., JP 2016-190646 A, JP 2016-131577A, etc.), a solution kit in which a container containing other component and a container containing a solution (corresponding to the composition) are integrated so as to communicate with each other (e.g., WO 96/25136, etc.), a double-chamber type prefilled syringe (e.g., JP 2012-245086A, etc.) and the like can be used.

In the electrolyte solution production method of the present invention, an example of the double-chamber container in which the composition and the other component are stored will be described with reference to FIG. 1. FIG. 1 is a cross-sectional view showing an example of a double-chamber container. As shown in FIG. 1, a double-chamber container includes a container 10, an electrolyte solution 11, and other component 21. The container 10 includes a first chamber 1 in which the electrolyte solution 11 is stored, a second chamber 2 in which other component 21 is stored, and an isolation portion 3 which isolates the first chamber 1 and the second chamber and allows the first chamber 1 and the second chamber 2 to communicate with each other. The container 10 further includes a hanging portion 5 with which the container 10 can be hanged.

As shown in FIG. 1, the container 10 is formed of a sheet 13, a sheet 14, and a discharge portion (discharge port) 22. As shown in FIG. 1, the sheet 14 is welded to the sheet 13 at the upper end to form an upper end portion 12 of the first chamber 1, and the sheet 13 and the sheet 14 are connected to the discharge portion 22 at the lower end. Further, the sheets 13 and 14 are welded at the center thereof to form the isolation portion 3. The welding of the isolating portion 3 is peelable, and the welding of the sheet 13 and the sheet 14 at the isolating portion 3 is released by applying pressure to the first chamber 1, so that the first chamber 1 and the second chamber 2 can communicate with each other. In the container 10, the first chamber 1 is a space from the upper end portion 12 to the isolation portion 3 in the sheet 13 and the sheet 14. In the container 10, the second chamber 2 is a space from the separation portion 3 to the discharge portion 22 in the sheet 13 and the sheet 14.

Plastic sheets can be used as the sheet 13 and the sheet 14. The plastic sheet is preferably composed of a plurality of layers, and includes an inner surface layer, an outer surface layer, and an intermediate layer, for example. As the inner surface layer and the outer surface layer, for example, a thermoplastic resin such as a thermoplastic olefin-based resin, a thermoplastic propylene-based resin, or a thermoplastic polyethylene-based resin can be used. Using such a thermoplastic resin, the sheet 13 and the sheet 14 are provided facing each other, and by performing heat sealing, the outer peripheral portions of the first chamber 1 and the second chamber 2, the upper end portion 12, and the isolating portion 3 can be easily formed, thereby producing the container 10. For example, a resin having high flexibility is preferred for the intermediate layer, and as a specific example, a thermoplastic olefin-based resin composition can be used.

The volume and shape of the first chamber 1 and the second chamber 2 are not particularly limited, and can be appropriately determined, for example, according to the dosage of the electrolyte solution 11 and other component.

The electrolyte solution production method of the present invention may include the step of sterilizing the electrolyte solution. The electrolyte solution-sterilizing can be carried out, for example, by performing sterilization treatment according to an indicator of the terminal sterilization method of the Japanese Pharmacopoeia, and the obtained electrolyte solution can be used as a final product.

<First Micro Bubble-Containing Solvent Production Method>

As described above, the method for producing a micro bubble-containing solvent used for preparing a micro bubble-containing electrolyte solution of the present invention includes the step of: filtrating a micro bubble-containing solvent with a filter medium, wherein a cation concentration in the micro bubble-containing solvent is less than 20 mmol/l, and the method satisfies at least one of the following conditions (4), (5) and (6):

Condition (4):

a micro bubble density in the micro bubble-containing solvent is $1\times10^6$ bubbles/ml or more;

Condition (5):

the method includes the step of preparing a micro bubble-containing solvent by introducing micro bubbles into a solvent; and Condition (6):

a micro bubble density in a filtrate is $1\times10^5$ bubbles/ml or more.

The first micro bubble-containing solvent production method of the present invention is characterized in that a cation concentration in a micro bubble-containing solvent to be subjected to the filtrating is set to less than 20 mmol/l, and other steps and conditions are not particularly limited. According to the first micro bubble-containing solvent production method of the present invention, since a decrease in micro bubbles during filtration can be suppressed, a decrease in micro bubble density in the obtained filtrate can be suppressed as compared with a case where the micro bubble-containing electrolyte solution is filtered. Accordingly, according to the first micro bubble-containing solvent production method of the present invention, it is possible to produce a micro bubble-containing solvent used for preparing an electrolyte solution which can contain a high concentration of micro bubbles. Regarding the first micro bubble-containing solvent production method of the present invention, reference can be made to the description as to the electrolyte solution production method of the present invention. Since the first micro bubble-containing solvent production method of the present invention can suppress a decrease in micro bubbles during filtration, it can also be referred to as a method for suppressing a decrease in micro bubbles in filtration.

In the first micro bubble-containing solvent production method of the present invention, in the filtrating, the micro bubble-containing solvent is subjected to filtration. Thus, the first micro bubble-containing solvent production method of the present invention may include the step of preparing a micro bubble-containing solvent by introducing micro bubbles into a solvent. In other words, the first micro bubble-containing solvent production method of the present invention may satisfy the condition (5). Regarding the solvent-preparing, reference can be made to the description as to the solvent-preparing in the electrolyte solution production method of the present invention.

The micro bubble density in the micro bubble-containing solvent obtained in the solvent-preparing is not particularly limited, and is increased as compared with the micro bubble density in the solvent before the solvent-preparing. Further, the micro bubble density in the micro bubble-containing solvent obtained in the solvent-preparing may be set according to, for example, the degree of a decrease in micro bubbles in the filtrating and a desired micro bubble density in the electrolyte solution.

The micro bubble density in the micro bubble-containing solvent is, for example, $1\times10^6$ bubbles/ml or more. In other words, the micro bubble density in the micro bubble-containing solvent satisfies, for example, the condition (4). The lower limit of the micro bubble density in the micro bubble-containing solvent is preferably $5\times10^6$ bubbles/ml, $1\times10^7$ bubbles/ml, $5\times10^7$ bubbles/ml, $1\times10^8$ bubbles/ml, $5\times10^8$ bubbles/ml, or $1\times10^9$ bubbles/ml, and more preferably $1\times10^6$ bubbles/ml, $5\times10^8$ bubbles/ml, $1\times10^7$ bubbles/ml, $5\times10^7$ bubbles/ml, $1\times10^8$ bubbles/ml, or $5\times10^8$ bubbles/ml. The upper limit of the micro bubble density in the micro bubble-containing solvent is, for example, $1.5\times10^9$ bubbles/ ml, $2\times10^9$ bubbles/ml, $3\times10^9$ bubbles/ml, $5\times10^9$ bubbles/ml, $7\times10^9$ bubbles/ml, $9\times10^9$ bubbles/ml, $1\times10^{10}$ bubbles/ml, $5\times10^{10}$ bubbles/ml, $1\times10^{11}$ bubbles/ml, $5\times10^{11}$ bubbles/ml, $1\times10^{12}$ bubbles/ml, or $5\times10^{12}$ bubbles/ml. The micro bubble density in the micro bubble-containing solvent is in the range, for example, from $1\times10^6$ bubbles/ml to $1\times10^{12}$ bubbles/ml, from $1\times10^6$ bubbles/ml to $1\times10^{11}$ bubbles/ml, from $1\times10^6$ bubbles/ml to $5\times10^{10}$ bubbles/ml, from $1\times10^6$ bubbles/ml to $1\times10^{10}$ bubbles/ml, from $1\times10^6$ bubbles/ml to $9\times10^9$ bubbles/ml, from $5\times10^6$ bubbles/ml to $9\times10^9$ bubbles/ml, from $1\times10^7$ bubbles/ml to $7\times10^9$ bubbles/ml, from $5\times10^7$ bubbles/ml to $7\times10^9$ bubbles/ml, from $1\times10^8$ bubbles/ml to $5\times10^9$ bubbles/ml, from $5\times10^8$ bubbles/ml to $5\times10^9$ bubbles/ml, from $1\times10^9$ bubbles/ml to $3\times10^9$ bubbles/ml, from $5\times10^8$ bubbles/ml to $2\times10^9$ bubbles/ml, or from $5\times10^8$ bubbles/ml to $1.5\times10^9$ bubbles/ml.

The first micro bubble-containing solvent production method of the present invention may include the step of adjusting a cation concentration in the micro bubble-containing solvent to less than 20 mmol/l prior to the filtrating if the cation concentration in the micro bubble-containing solvent before or after the solvent-preparing does not satisfy the aforementioned numerical range. Regarding the concentration-adjusting, reference can be made to the description as to the concentration-adjusting in the electrolyte solution production method of the present invention.

Next, in the filtrating, a micro bubble-containing solvent is filtered with a filter medium. Regarding the filtrating, reference can be made to the description as to the filtrating in the electrolyte solution production method of the present invention.

The micro bubble density in the filtrate obtained in the filtrating is not particularly limited, and, for example, the density is $1\times10^5$ bubbles/ml or more (condition (6)). The lower limit of the micro bubble density in the filtrate is preferably $1\times10^6$ bubbles/ml, $5\times10^6$ bubbles/ml, $1\times10^7$ bubbles/ml, $5\times10^7$ bubbles/ml, $1\times10^8$ bubbles/ml, $5\times10^8$ bubbles/ml, or $1\times10^8$ bubbles/ml, and preferably $1\times10^6$ bubbles/ml, $5\times10^6$ bubbles/ml, $1\times10^7$ bubbles/ml, $5\times10^7$ bubbles/ml, $1\times10^8$ bubbles/ml, or $5\times10^8$ bubbles/ml, for example, because the electrolyte solution prepared from the filtrate can be suitably used as a low material liquid such as a preservation solution, a culture solution, or an infusion. The upper limit of the micro bubble density in the electrolyte solution is, for example, $1.5\times10^8$ bubbles/ml, $2\times10^8$ bubbles/ml, $3\times10^8$ bubbles/ml, $5\times10^8$ bubbles/ml, $7\times10^8$ bubbles/ml, $9\times10^9$ bubbles/ml, $1\times10^{10}$ bubbles/ml, $5\times10^{10}$ bubbles/ml, $1\times10^{11}$ bubbles/ml, $5\times10^{11}$ bubbles/ml, $1\times10^{12}$ bubbles/ml, or $5\times10^{12}$ bubbles/ml. The micro bubble density in the electrolyte solution is in the range, for example, from $1\times10^5$ bubbles/ml to $5\times10^{12}$ bubbles/ml, from $5\times10^5$ bubbles/ml to $5\times10^{12}$ bubbles/ml, from $5\times10^5$ bubbles/ml to $1\times10^{12}$ bubbles/ml, from $5\times10^5$ bubbles/ml to $5\times10^{11}$ bubbles/ml, from $5\times10^5$ bubbles/ml to $1\times10^{11}$ bubbles/ml, from $5\times10^5$ bubbles/ml to $5\times10^{10}$ bubbles/ml, from $5\times10^5$ bubbles/ml to $1\times10^{10}$ bubbles/ml, from $1\times10^6$ bubbles/ml to $9\times10^9$ bubbles/ml, from $5\times10^6$ bubbles/ml to $9\times10^9$ bubbles/ml, from $1\times10^7$ bubbles/ml to $7\times10^9$ bubbles/ml, from $5\times10^7$ bubbles/ml to $7\times10^9$ bubbles/ml, from $1\times10^8$ bubbles/ml to $5\times10^9$ bubbles/ml, from $5\times10^8$ bubbles/ml to $5\times10^9$ bubbles/ml, from $1\times10^9$ bubbles/ml to $3\times10^9$ bubbles/ml, from $5\times10^8$ bubbles/ml to $2\times10^9$ bubbles/ml, or from $5\times10^8$ bubbles/ml to $1.5\times10^9$ bubbles/ml.

The first micro bubble-containing solvent production method of the present invention may satisfy any one or more of the conditions (4) to (6), and satisfies one, two, or three of them. The first micro bubble-containing solvent production method of the present invention preferably satisfies the condition (6) because, for example, the electrolyte solution prepared from the filtrate can be suitably used as a preservation solution, a culture solution, or an infusion.

In the first micro bubble-containing solvent production method of the present invention, the micro bubble-containing solvent may be filled into a container (the solvent-filling). Thereby, the micro bubble-containing solvent can be easily transported and stored. The method of filling the container can be appropriately determined according to, for example, the form of the container. Regarding the solvent-filling, reference can be made to the description as to the electrolyte solution-filling in the electrolyte solution production method of the present invention by reading the "electrolyte solution" as the "micro bubble-containing solvent".

The first micro bubble-containing solvent production method of the present invention may include the step of sterilizing the micro bubble-containing solvent. The micro bubble-containing solvent-sterilizing can be carried out, for example, by performing sterilization treatment according to an indicator of the terminal sterilization method of the Japanese Pharmacopoeia, and the obtained micro bubble-containing solvent can be used as a final product.

<Second Micro Bubble-Containing Solvent Production Method>

The second method for producing a micro bubble-containing solvent used for preparing a micro bubble-containing electrolyte solution of the present invention (hereinafter, also referred to as the "second micro bubble-containing solvent production method") includes the steps of: adjusting a cation concentration in a micro bubble-containing solvent to less than 20 mmol/l; and filtrating the adjusted solvent with a filter medium. The second micro bubble-containing solvent production method of the present invention is characterized in that a cation concentration in a micro bubble-containing solvent to be subjected to the filtrating is set to less than 20 mmol/l, and other steps and conditions are not particularly limited. Regarding the second micro bubble-containing solvent production method of the present invention, reference can be made to the description as to the electrolyte solution production method and first micro bubble-containing solvent production method of the present invention. According to the second micro bubble-containing solvent production method of the present invention, since a decrease in micro bubbles during filtration can be suppressed, a decrease in micro bubble density in the obtained filtrate can be suppressed as compared with a case where the micro bubble-containing electrolyte solution is filtered. Accordingly, according to the second micro bubble-containing solvent production method of the present invention, it is possible to produce a micro bubble-containing solvent used for preparing an electrolyte solution which can contain a high concentration of micro bubbles. Regarding the second micro bubble-containing solvent production method of the present invention, reference can be made to the description as to the electrolyte solution production method of the present invention. Since the second micro bubble-containing solvent production method of the present invention can suppress a decrease in micro bubbles during filtration, it can also be referred to as a method for suppressing a decrease in micro bubbles in filtration.

In the second micro bubble-containing solvent production method of the present invention, in the filtrating, the micro bubble-containing solvent is subjected to filtration. Thus, the second micro bubble-containing solvent production method of the present invention may include the step of preparing a micro bubble-containing solvent by introducing micro bubbles into a solvent. In other words, the first micro bubble-containing solvent production method of the present invention may satisfy the condition (5). Regarding the solvent-preparing, reference can be made to the description as to the solvent-preparing in the electrolyte solution production method of the present invention. The solvent-preparing may be performed before or after the concentration-adjusting.

Next, in the concentration-adjusting, the cation concentration in the micro bubble-containing solvent is adjusted to less than 20 mmol/l. Specifically, first, in the concentration-adjusting, the cation concentration in the micro bubble-containing solvent is measured. When the second micro bubble-containing solvent production method of the present invention includes the solvent-preparing, in the concentration-adjusting, the cation concentration in the micro bubble-containing solvent before or after the solvent-preparing is measured. Regarding the method for measuring the cation concentration, reference can be made to the description described above. Then, in the concentration-adjusting, when the cation concentration in the micro bubble-containing solvent is 20 mmol/l or more, for example, the micro bubble-containing solvent before or after the solvent-preparing is diluted by a solvent (dilution solvent). The dilution solvent may be, for example, the same as or different from the solvent in the micro bubble-containing solvent, and is preferably the same. The dilution solvent is preferably an aqueous solvent, and more preferably water, distilled water, or pure water. The cation concentration in the dilution solvent is less than 20 mmol/l. Regarding the cation concentration in the dilution solvent, for example, reference can be made to the cation concentration in the micro bubble-containing solvent of the electrolyte solution production method of the present invention.

Regarding the micro bubble density in the micro bubble-containing solvent, for example, reference can be made to the description as to the micro bubble density in the micro bubble-containing solvent in the first micro bubble-containing solvent production method of the present invention.

Next, in the filtrating, a micro bubble-containing solvent is filtered with a filter medium. Regarding the filtrating, reference can be made to the description as to the filtrating in the electrolyte solution production method of the present invention. Regarding the micro bubble density in the filtrate, for example, reference can be made to the description as to the micro bubble density in the filtrate in the first micro bubble-containing solvent production method of the present invention.

The second micro bubble-containing solvent production method of the present invention may satisfy any one or more of the conditions (4) to (6), and satisfies one, two, or three of them. The first micro bubble-containing solvent production method of the present invention preferably satisfies the condition (6) because, for example, the electrolyte solution prepared from the filtrate can be suitably used as a preservation solution, a culture solution, or an infusion.

In the second micro bubble-containing solvent production method of the present invention, the micro bubble-containing solvent may be filled into a container (the solvent-filling). Thereby, the micro bubble-containing solvent can be easily transported and stored. The method of filling the container can be appropriately determined according to, for example, the form of the container. Regarding the solvent-filling, reference can be made to the description as to the electrolyte solution-filling in the electrolyte solution production method of the present invention by reading the "electrolyte solution" as the "micro bubble-containing solvent".

The second micro bubble-containing solvent production method of the present invention may include the step of sterilizing the micro bubble-containing solvent. The micro bubble-containing solvent-sterilizing can be carried out, for example, by performing sterilization treatment according to an indicator of the terminal sterilization method of the Japanese Pharmacopoeia, and the obtained micro bubble-containing solvent can be used as a final product.

EXAMPLES

The examples of the present invention are described below. The present invention, however, is not limited by the following examples.

Example 1

The present example examined that decrease in micro bubbles during filtration can be suppressed by setting the electrolyte concentration to a predetermined concentration or less using electrolytes generating different cations.

(1) Production of Micro Bubble-Containing Solvent

Figure 2:
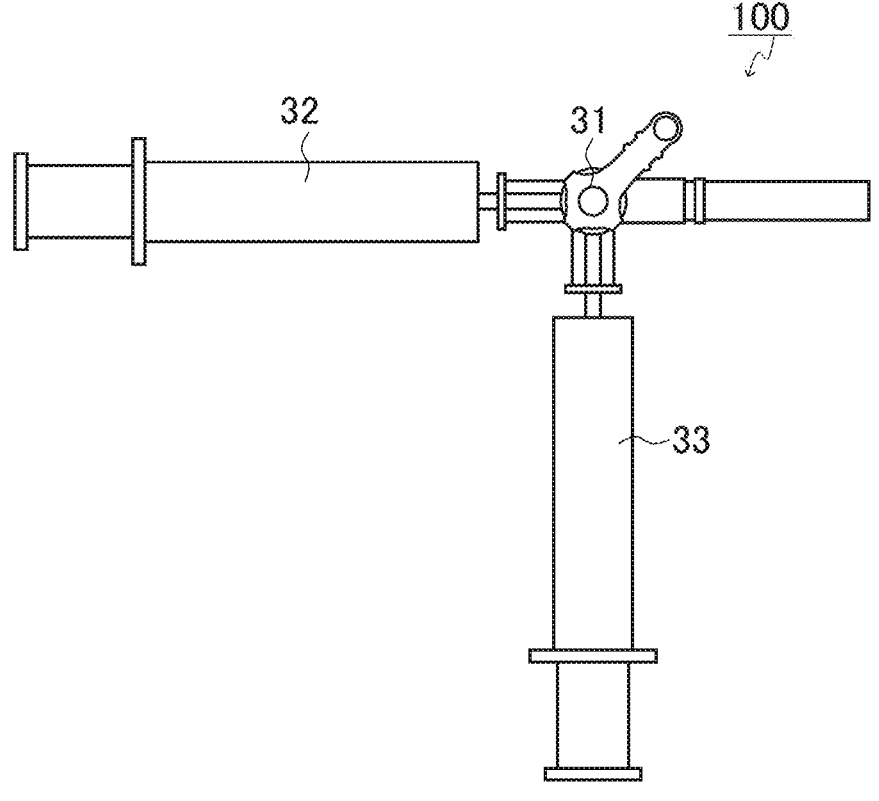
FIG. 2 is a schematic diagram showing a micro bubble production apparatus in Example 1.

The composition of the present invention was produced using a micro bubble production apparatus 100 shown in FIG. 2. As shown in FIG. 2, the production apparatus 100 includes syringes 32 and 33 disposed on two sides of a three-way stopcock 31. In the production apparatus 100, the syringes 32 and 33 communicate with each other via the three-way stopcock 31. First, the syringe 32 was released from the three-way stopcock 31, and 20 ml of an electrolyte solution was introduced into the inside thereof. The electrolyte solution will be described below. Next, the syringe 32 was again connected to the three-way stopcock 31 to remove the gas in the three-way stopcock 31. After the removal, the syringe 33 was released from the three-way stopcock 31 to introduce 20 ml of air into the inside thereof. Then, the syringe 33 was again connected to the three-way stopcock 31. After the connection, micro bubbles containing air as a gas component were produced by continuously pistoning each plunger of the syringes 32 and 33 in each outer cylinder of the syringes 32 and 33 for 10 minutes, thereby producing a micro bubble-containing solvent. It has been checked that the main component of the micro bubble is an ultrafine bubble in the measurement of the micro bubble density, which will be described below.

Sodium chloride (NaCl), potassium chloride (KCl), calcium chloride ($CaCl_2$)), or aluminium chloride ($AlCl_3$) was added to distilled water to obtain an electrolyte solution having a predetermined concentration. The final concentration of the sodium chloride was 0.17, 1.7, or 17 mmol/l. The final concentration of the potassium chloride was 0.1, 1, or 10 mmol/l. The final concentration of the calcium chloride was 0.01, 0.1, 1, or 10 mmol/l. The final concentration of the aluminum chloride was 0.01, 0.01, or 0.1 mmol/l. Further, an electrolyte solution to which sodium chloride was added and an electrolyte solution to which potassium chloride was added were mixed at 1:1 to prepare an electrolyte solution. These electrolyte solutions were used to produce micro bubble-containing solvents.

(2) Filtration of Micro Bubble-Containing Solvent

Figure 3:
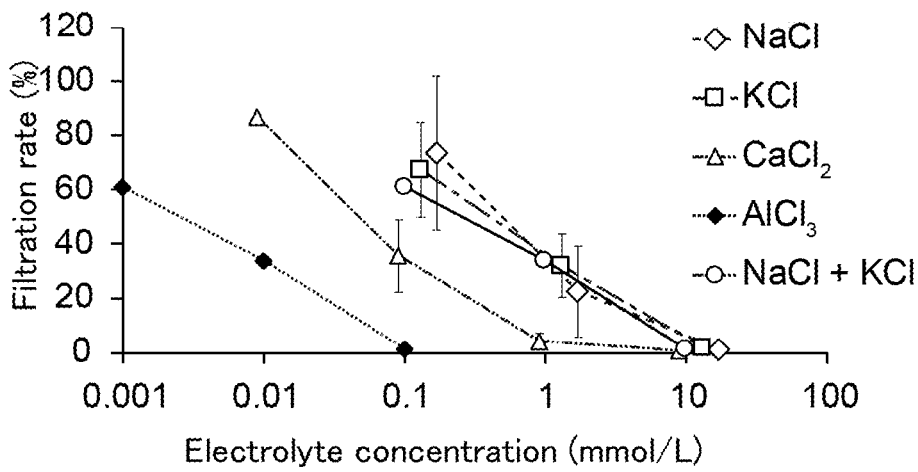
FIG. 3 is a graph showing the filtration rate at the concentrations of the electrolyte in Example 1.

Next, after the bubbles which can be observed by the naked eye disappear, a micro bubble-containing solvent containing each electrolyte was filtered using a syringe filter (Millex-GV, produced by Millipore, Cat. No.: SLGV033RS) provided with a PVDF membrane having an absolute pore diameter of 0.22 m (220 nm). After the filtration, the micro bubble density of each of the micro bubble-containing solvents before and after the filtration was measured using a NanoSight® NS300 (produced by Malvern Instrument) with a default parameter. Incidentally, the measurement was performed at 25° C. Then, the filtration rate ($F_R$) was calculated from the micro bubble density ($F_A$) in the micro bubble-containing solvent after filtration based on the micro bubble density ($F_B$) in the micro bubble-containing solvent before filtration (100%), using Equation (1) below. The results thereof are shown in FIG. 3. The micro bubble density in the micro bubble-containing solvent before filtration was 0.5 to $1 \times 10^{10}$ bubbles/ml.

$$F_R = F_A / F_B \times 100 (\%) \tag{1}$$

FIG. 3 is a graph showing the filtration rate of the electrolyte at each concentration. As shown in FIG. 3, the horizontal axis indicates the electrolyte concentration, and the vertical axis indicates the filtration rate. As shown in FIG. 3, in the micro bubble-containing solvent containing any electrolyte, the filtration rate decreased in an electrolyte concentration-dependent manner. It was found that, in a micro bubble-containing solvent containing sodium chloride (NaCl), potassium chloride (KCl), or sodium chloride and potassium chloride (NaCl+KCl), the filtration rate becomes about 0% at about 20 mmol/l, and the filtration rate was improved by setting the concentration less than 20 mmol/l. It was found that, in a micro bubble-containing containing calcium chloride ($CaCl_2$)), the filtration rate becomes about 0% at 10 mmol/l, and the filtration rate was improved by setting the concentration less than 10 mmol/l. It was found that the filtration rate of the micro bubble-containing solvent containing aluminium chloride ($AlCl_3$) was about 0% at 0.1 mmol/l, and the filtration rate was improved by setting the concentration less than 0.1 mmol/l. These results show that the electrolyte inhibits the filtration of the micro bubbles in the micro bubble-containing solvent, and that a decrease in micro bubbles during filtration can be suppressed by setting the electrolyte concentration to a predetermined concentration or less.

Example 2

The present example examined that a decrease in micro bubbles during filtration can be suppressed by setting the cation concentration to a predetermined concentration or less using electrolytes generating different anions.

(1) Production of Micro Bubble-Containing Solvent

A micro bubble-containing solvent was produced in the same manner as in (1) in Example 1. Sodium chloride (NaCl), sodium carbonate ($Na_2CO_3$), or disodium hydrogenphosphate ($Na_2HPO_3$) was added to distilled water to obtain an electrolyte solution for using the micro bubble-containing solvent production having a predetermined concentration. The final concentration of the sodium chloride was 0.17, 1.7, or 17 mmol/l. The final concentration of the sodium carbonate was 0.1, 1, or 10 mmol/l. The final concentration of disodium hydrogen phosphate was 0.01, 0.1, 1, or 10 mmol/l.

(2) Filtration of Micro Bubble-Containing Solvent

Figure 4:
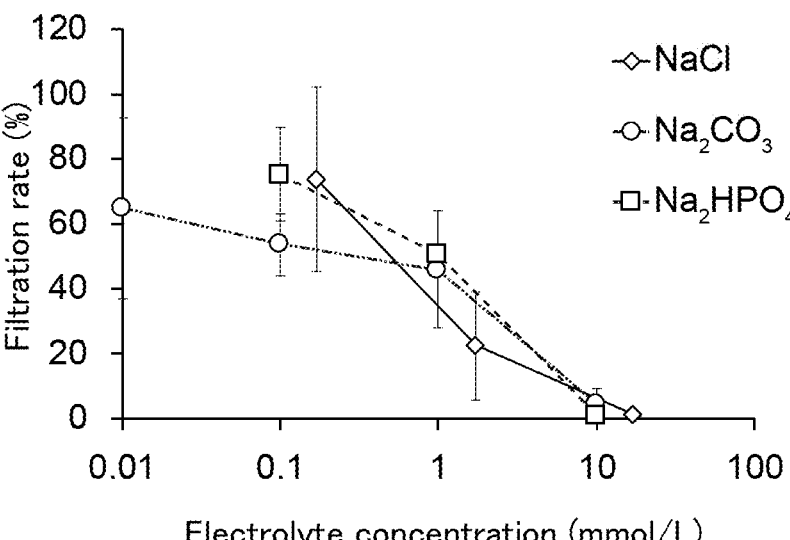
FIG. 4 is a graph showing the filtration rate at the concentrations of the electrolyte in Example 2.

Next, filtration was performed in the same manner as in (2) in Example 1, except that the micro bubble-containing solvent obtained in (1) in Example 2 was used instead of the micro bubble-containing solvent obtained in (1) in Example 1. After the filtration, the micro bubble density of each of the micro bubble-containing solvents before and after the filtration was measured in the same manner as in (2) in Example 1. Then, the filtration rate ($F_R$) was calculated from the micro bubble density ($F_A$) in the micro bubble-containing solvent after filtration based on the micro bubble density $(F_B)$ in the micro bubble-containing solvent before filtration (100%), using the Equation (1). The results thereof are shown in FIG. 4. The micro bubble density in the micro bubble-containing solvent before filtration was 0.5 to $1\times10^{10}$ bubbles/ml.

FIG. 4 is a graph showing the filtration rate of the electrolyte at each concentration. As shown in FIG. 4, the horizontal axis indicates the electrolyte concentration, and the vertical axis indicates the filtration rate. As shown in FIG. 4, in the micro bubble-containing solvent containing any electrolyte, the filtration rate decreased in an electrolyte concentration-dependent manner. It was found that, in a micro bubble-containing solvent containing sodium chloride, the filtration rate becomes about 0% at about 20 mmol/l, and the filtration rate was improved by setting the concentration less than 20 mmol/l. It was found that the filtration rate of the micro bubble-containing solvent containing sodium carbonate or disodium hydrogenphosphate was about 0% at about 10 mmol/l, and the filtration rate was improved by setting the concentration less than 10 mmol/l.

When sodium chloride is dissolved in a solvent, the sodium chloride ionizes into one sodium ion and one chloride ion. When sodium carbonate is dissolved in a solvent, the sodium carbonate ionizes into two sodium ions and one carbonate ion. When disodium hydrogen phosphate is dissolved in a solvent, the disodium hydrogen phosphate ionizes into two sodium ions and one hydrogen phosphate ion. Therefore, the anion concentration in the micro bubble-containing solvent containing sodium chloride and the anion concentration in the micro bubble-containing solvent containing sodium carbonate or disodium hydrogen phosphate are approximate concentrations. On the other hand, the cation concentration in the micro bubble-containing solvent containing sodium chloride is at about the half of the cation concentration in the micro bubble-containing solvent containing sodium carbonate or disodium hydrogen phosphate. In addition, since sodium carbonate or disodium hydrogen phosphate can achieve a filtration rate of 0% of micro bubbles at a concentration of about the half of sodium chloride, it was found that a sodium ion, which is a cation, mainly affects the filtration rate of micro bubbles.

These results show that a decrease in micro bubbles during filtration can be suppressed by setting the cation concentration to a predetermined concentration or less.

Example 3

The present example examined, in filter media of different absolute pore diameters, that micro bubbles are decreased during filtration by adding cations and that a decrease in micro bubbles during filtration can be suppressed by lowering the cation concentration.

(1) Production of Micro Bubble-Containing Solvent

A micro bubble-containing solvent was produced in the same manner as in (1) in Example 1, except that distilled water was used instead of the electrolyte solution. Next, sodium chloride (NaCl) was added to the micro bubble-containing solvent so as to have a concentration of 0.9 w/v %, thereby producing a micro bubble-containing physiological saline solution.

(2) Filtration of Micro Bubble-Containing Solvent

Next, filtration was performed in the same manner as in (2) in Example 1, except that the micro bubble-containing physiological saline solution obtained in (1) in Example 3 was used instead of the micro bubble-containing solvent to which the electrolyte was added obtained in (1) in Example 1, and that in addition to a syringe filter having an absolute pore diameter of 0.22 μm (220 nm), a syringe filter having an absolute pore diameter of 0.1 μm (100 nm) (Millex-VV, produced by Millipore, Cat. No.: SLVV033RS) or a syringe filter having an absolute pore diameter of 0.45 μm (450 nm) (Millex-HV, produced by Millipore, Cat. No.: SLHV033RS) was used. After the filtration, the micro bubble density of each of the micro bubble-containing physiological saline solutions before and after the filtration was measured in the same manner as in (2) in Example 1. Then, the filtration rate $(F_R)$ was calculated from the micro bubble density $(F_A)$ in the micro bubble-containing solvent after filtration based on the micro bubble density $(F_B)$ in the micro bubble-containing solvent before filtration (100%), using the Equation (1). In addition, the filtration rate $(F_R)$ was calculated in the same manner except that the micro bubble-containing solvents to which no sodium chloride was added were used. The results thereof are shown in FIGS. 5A and 5B. The micro bubble density in the micro bubble-containing solvent before filtration was 0.5 to $1\times10^{10}$ bubbles/ml.

FIGS. 5A and 5B are graphs showing the filtration rate in the micro bubble-containing physiological saline solution and in a micro bubble-containing solvent to which no sodium chloride was added. FIG. 5A shows the results of the micro bubble-containing physiological saline solution, and FIG. 5B shows the results of the micro bubble-containing solvent to which no sodium chloride was added. In FIGS. 5A and 5B, the horizontal axis indicates the absolute pore diameter of the syringe filter, and the vertical axis indicates the filtration rate. As shown in FIG. 5A, in the micro bubble-containing physiological saline solution, the filtration rate was almost 0% even in the case of using a syringe filter having any absolute pore diameter. On the other hand, as shown in FIG. 5B, in the micro bubble-containing solvent to which no sodium chloride was added, a decrease in the filtration rate was suppressed as compared with a micro bubble-containing physiological saline solution even in the case of using a syringe filter having any absolute pore diameter. It is considered that, since there are micro bubbles bigger than an absolute pore diameter of the filter in the micro bubble-containing physiological saline solution, the filtration rate fluctuates in the absolute pore diameter-dependent manner.

From the above, it was found that even in the filter media of different absolute pore diameters, the filtration of the micro bubbles is decreased by the addition of cations.

Example 4

The present example examined, in micro bubble-containing solvents obtained by different micro bubble production methods, that micro bubbles are decreased during filtration by adding cations and that a decrease in micro bubbles during filtration can be suppressed by lowering the cation concentration during filtration.

(1) Production of Micro Bubble-Containing Solvent

Figure 6:
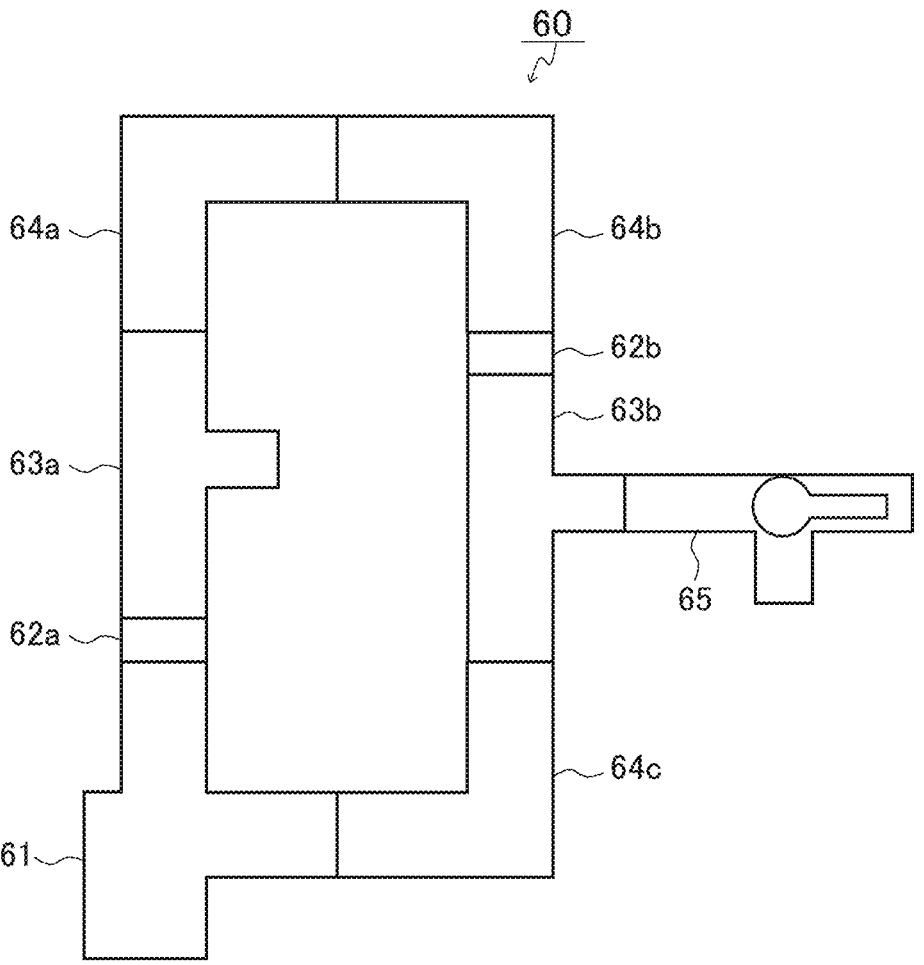
FIG. 6 is a schematic view showing a micro bubble production apparatus in Example 4.

A micro bubble-containing solvent was produced in the same manner as in (1) in Example 1 (syringe type). Next, a micro bubble-containing solvent was produced using a venturi-type micro bubble production apparatus 60 shown in FIG. 6 (closed circulation type). As shown in FIG. 6, the production apparatus 60 has a circulation system flow path in which a tube 62a, a venturi tube 63a, connecting tubes 64a and 64b, a tube 62b, a venturi tube 63b, and a connecting tube 64c are connected in this order to communicate with each other with reference to a motor 61. An opening formed in a protrusion at the side surface of the venturi tube 63a is sealed. Further, an opening formed in a protrusion at the side surface of the venturi pipe 63b is connected to a three-way stopcock 65 so as to communicate with each other. First, the three-way stopcock 65 was opened to introduce distilled water from the three-way stopcock 65 into the flow path in the production apparatus 60. At this time, the flow path was filled with the distilled water so as not to contain a gas. The liquid amount of the filled distilled water was also measured. Next, air was introduced into the flow path so as to be about 20 ml (about 10 ml gas/50 ml solvent (distilled water)) with respect to 100 ml of distilled water introduced, and then the three-way stopcock 65 was closed. Then, by circulating the distilled water and air in the flow path for 5 minutes using the motor 61, micro bubbles were formed, thereby producing a micro bubble-containing solvent. The flow rate at which the distilled water was circulated by the motor 61 was 3.6 l/min.

Next, sodium chloride (NaCl) was added to each micro bubble-containing solvent so as to have a concentration of 0.9 w/v %, thereby producing a micro bubble-containing physiological saline solution.

(2) Filtration of Micro Bubble-Containing Solvent

Figure 7A:
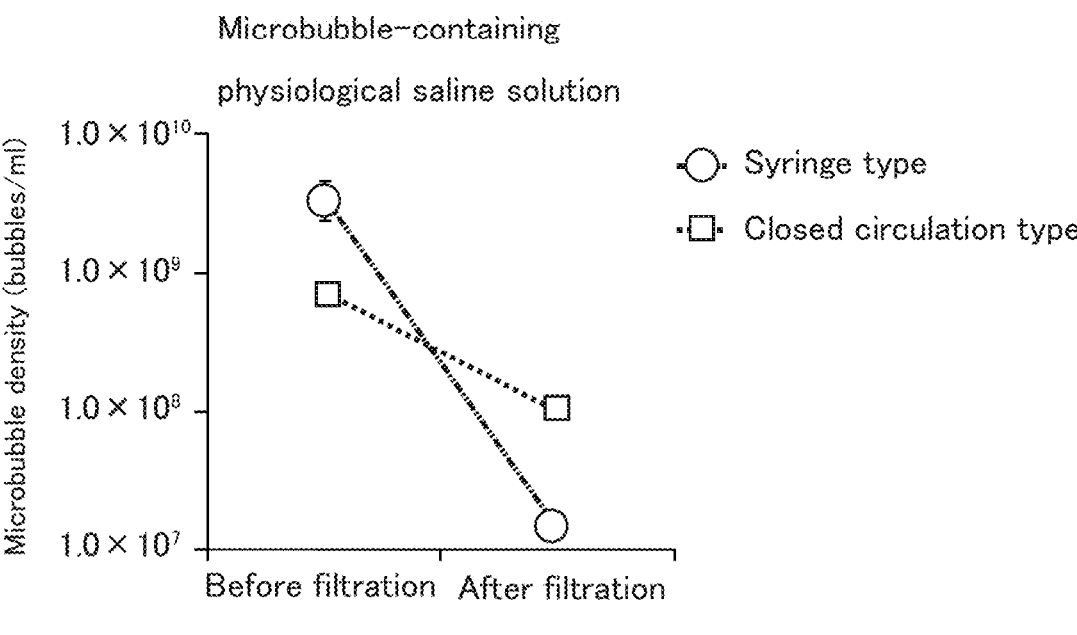
FIGS. 7A and 7B are graphs showing the micro bubble density in Example 4.
Figure 7B:
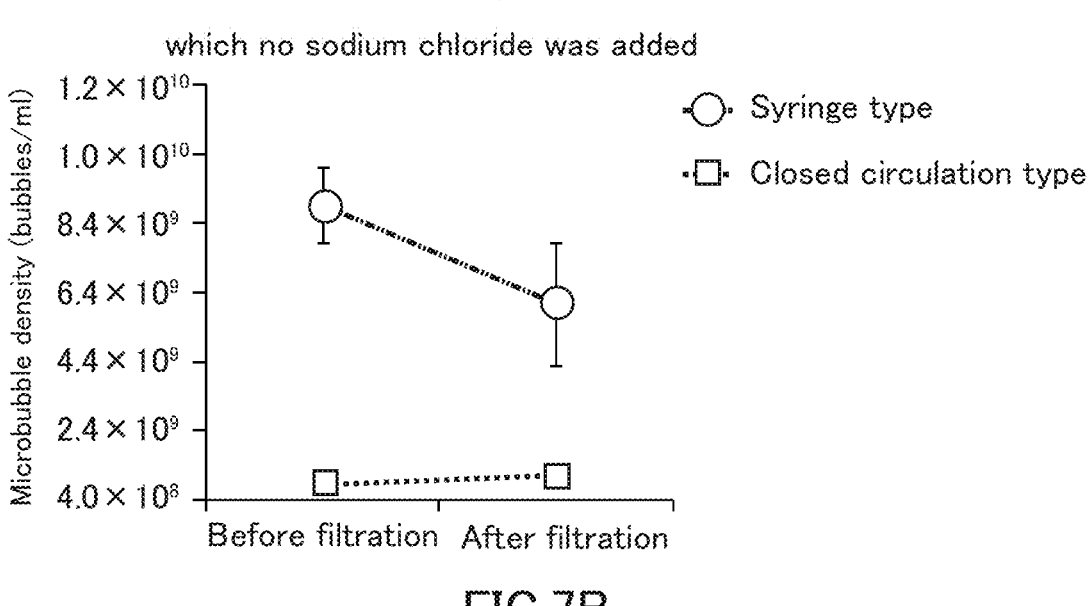

Next, filtration was performed in the same manner as in (2) in Example 1, except that the micro bubble-containing physiological saline solution obtained in (1) in Example 4 was used instead of the micro bubble-containing solvent to which the electrolyte was added obtained in (1) in Example 1. After the filtration, the micro bubble density of each of the micro bubble-containing physiological saline solutions before and after the filtration was measured in the same manner as in (2) in Example 1. The micro bubble density was measured in the same manner except that the micro bubble-containing solvents to which no sodium chloride was added were used. The results thereof are shown in FIGS. 7A and 7B. The micro bubble density in the micro bubble-containing solvent before filtration was 0.5 to 1×10¹⁰ bubbles/ml.

FIGS. 7A and 7B are graphs showing the micro bubble density. FIG. 7A shows the results of the micro bubble-containing physiological saline solution, and FIG. 7B shows the results of the micro bubble-containing solvent to which no sodium chloride was added. In FIGS. 7A and 7B, the horizontal axis indicates the time of acquisition of the sample subjected to measurement, and the vertical axis indicates the micro bubble density. As shown in FIG. 7A, regardless of the micro bubble production methods, by adding cation having a predetermined concentration or more, the micro bubbles were greatly decreased during filtration. On the other hand, as shown in FIG. 7B, regardless of the micro bubble production methods, when the cation concentration was less than a predetermined concentration, the decrease in the micro bubbles was suppressed during filtration. From these results, it was found that, regardless of the type of the micro bubble production method, in the obtained micro bubble-containing solvent the micro bubbles are decreased during filtration by adding cations and the decrease in micro bubbles can be suppressed by lowering the cation concentration during filtration.

Example 5

The present example examined, in micro bubble-containing solvents of different micro bubble densities, that micro bubbles are decreased during filtration by adding cations and that a decrease in micro bubbles can be suppressed by lowering the cation concentration during filtration.

(1) Production of Micro Bubble-Containing Solvent

A micro bubble-containing solvent was produced in the same manner as in (1) in Example 1, except that distilled water was used instead of the electrolyte solution. The micro bubble density of the obtained micro bubble-containing solvent was measured in the same manner as in (2) in Example 1. Based on the density obtained, the micro bubble-containing solvent was diluted with distilled water so as to achieve a micro bubble density of 1×10⁸ bubbles/ml or 1×10¹⁰ bubbles/ml. Sodium chloride was added to the micro bubble-containing solvent after dilution so as to achieve 0.9 w/v %, thereby preparing a micro bubble-containing physiological saline solution.

(2) Filtration of Micro Bubble-Containing Solvent

Figure 8:
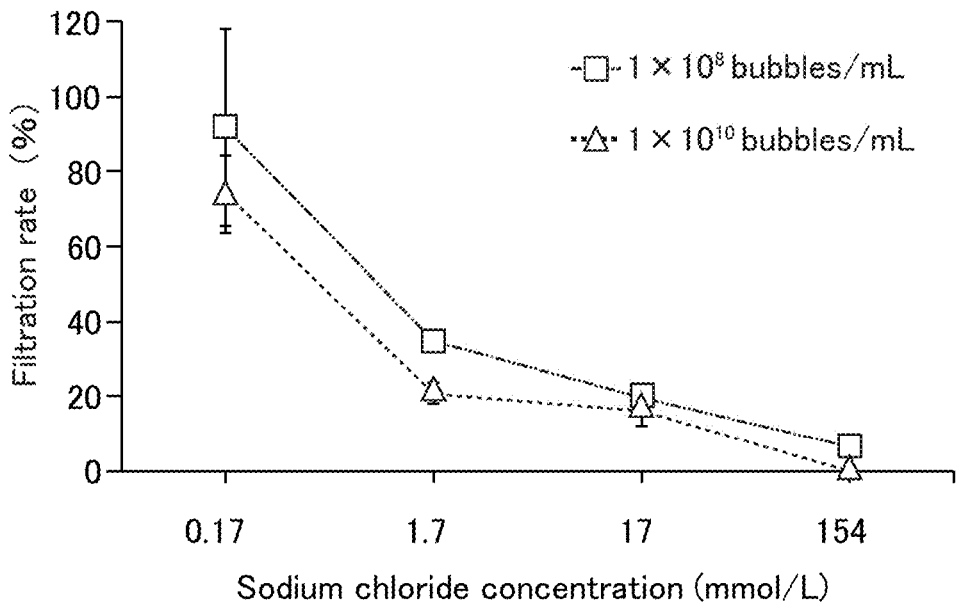
FIG. 8 is a graph showing the filtration rate in Example 5.

Next, filtration was performed in the same manner as in (2) in Example 1, except that the micro bubble-containing physiological saline solution obtained in (1) in Example 5 was used instead of the micro bubble-containing solvent to which the electrolyte was added obtained in (1) in Example 1. After the filtration, the micro bubble density of each of the micro bubble-containing physiological saline solutions before and after the filtration was measured in the same manner as in (2) in Example 1. Then, the filtration rate ($F_R$) was calculated from the micro bubble density ($F_A$) in the micro bubble-containing solvent after filtration based on the micro bubble density ($F_B$) in the micro bubble-containing solvent before filtration (100%), using the Equation (1). The results thereof are shown in FIG. 8. The micro bubble density in the micro bubble-containing solvent before filtration was 0.5 to 1×10¹⁰ bubbles/ml.

FIG. 8 is a graph showing the filtration rate. In FIG. 8, the horizontal axis indicates the concentration of sodium chloride, and the vertical axis indicates the filtration rate. As shown in FIG. 8, regardless of the micro bubble density in the micro bubble-containing solvent, the micro bubbles were decreased during filtration in a cation concentration-dependent manner. In addition, regardless of the micro bubble density in the micro bubble-containing solvent, the decrease in micro bubbles could be suppressed by lowering the cation concentration during filtration. From these results, it was found that, regardless of the micro bubble density in the micro bubble-containing solvent, micro bubbles during filtration was decreased by adding cations and a decrease in micro bubbles could be suppressed by lowering the cation concentration during filtration.

Example 6

The present example examined that a micro bubble-containing electrolyte solution can be produced by the electrolyte solution production method of the present invention using filters composed of different polymers.

(1) Production of Micro Bubble-Containing Solvent

A micro bubble-containing solvent was produced in the same manner as in (1) in Example 1 except that distilled water was used instead of the electrolyte solution.

(2) Filtration of Micro Bubble-Containing Solvent

Figure 9:
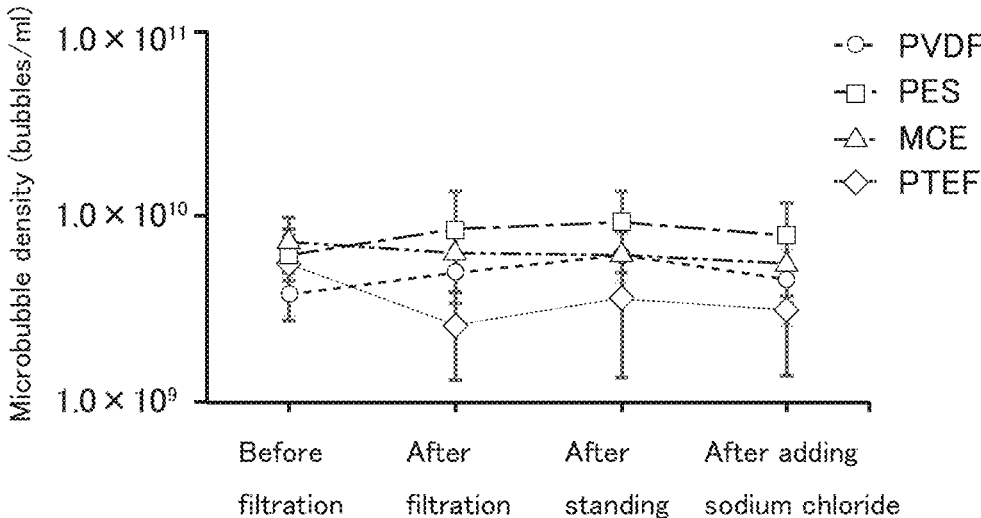
FIG. 9 is a graph showing the micro bubble density in Example 6.

Next, filtration was performed in the same manner as in (2) in Example 1, except that the micro bubble-containing solvent obtained in (1) in Example 6 was used instead of the micro bubble-containing solvent to which the electrolyte was added obtained in (1) in Example 1, and that a syringe filter ((absolute pore diameter) 220 nm, Millex-GV, produced by Millipore, Cat. No: SLGV033RS) provided with a PVDF membrane, a syringe filter ((absolute pore diameter) 220 nm, Millex-GP, produced by Millipore, Cat. No: SLGP033RS) provided with a PES membrane, a syringe filter ((absolute pore diameter) 220 nm, Millex-GS, produced by Millipore, Cat. No: SLGS033SS) provided with an MCE membrane, or a syringe filter ((absolute pore diameter) 220 nm, Millex-FG, produced by Millipore, Cat. No: SLFGJ25LS) provided with a PTFE membrane was used. After the filtration, the micro bubble-containing solvent was allowed to stand for 24 hours. After the standing, sodium chloride was added to the micro bubble-containing solvent so as to achieve 0.9 w/v %, thereby preparing a micro bubble-containing physiological saline solution. Then, the micro bubble density of the micro bubble-containing solvent before and after filtration, the micro bubble-containing solvent after standing, and the micro bubble-containing physiological saline solution was measured in the same manner as in (2) in Example 1. The results thereof are shown in FIG. 9. The micro bubble density in the micro bubble-containing solvent before filtration was 0.5 to $1 \times 10^{10}$ bubbles/ml.

FIG. 9 is a graph showing the micro bubble density. In FIG. 9, the horizontal axis indicates the time of acquisition of a target to be measurement, and the vertical axis indicates the micro bubble density. As is apparent from the comparison between before filtration and after filtration of FIG. 9, when the cation concentration was less than a predetermined concentration, the decrease in the micro bubbles during filtration was suppressed, regardless of the material of the filter. Thereby, the micro bubble density in the micro bubble-containing solvent was in the range from $1 \times 10^9$ to $1 \times 10^{10}$ bubbles/ml, even after filtration. Further, even when an electrolyte solution was prepared by adding an electrolyte to the micro bubble-containing solvent after filtration, the micro bubble density in the electrolyte solution hardly changed as compared with before the addition of the electrolyte. From the above, it was found that, according to the electrolyte solution production method of the present invention, a micro bubble-containing electrolyte solution containing a high concentration of micro bubbles can be produced.

While the present invention has been described above with reference to illustrative example embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2019-196792 filed on Oct. 29, 2019. The entire subject matter of the Japanese Patent Applications is incorporated herein by reference.

(Supplementary Notes)

Some or all of the above example embodiments and examples may be described as in the following Supplementary Notes, but are not limited thereto.

(Supplementary Note 1)

A method for producing a micro bubble-containing electrolyte solution, including the steps of:

filtrating a micro bubble-containing solvent with a filter medium; and preparing an electrolyte solution from the obtained filtrate, wherein a cation concentration in the micro bubble-containing solvent is less than 20 mmol/l, and the method satisfies at least one of the following conditions (1), (2) and (3):

Condition (1):

a micro bubble density in the micro bubble-containing solvent is $1 \times 10^6$ bubbles/ml or more;

Condition (2):

the method includes the step of preparing the micro bubble-containing solvent by introducing micro bubbles into a solvent; and Condition (3):

a micro bubble density in the electrolyte solution is $1 \times 10^5$ bubbles/ml or more.

(Supplementary Note 2)

The method for producing a micro bubble-containing electrolyte solution according to Supplementary Note 1, wherein the cation is a monovalent cation.

(Supplementary Note 3)

The method for producing a micro bubble-containing electrolyte solution according to Supplementary Note 2, wherein the monovalent cation is at least one of a sodium ion or a potassium ion.

(Supplementary Note 4)

The method for producing a micro bubble-containing electrolyte solution according to any one of Supplementary Notes 1 to 3, wherein the filter medium has an absolute pore diameter of 100 to 450 nm.

(Supplementary Note 5)

The method for producing a micro bubble-containing electrolyte solution according to any one of Supplementary Notes 1 to 3, wherein the filter medium has an absolute pore diameter of 50 to 220 nm.

(Supplementary Note 6)

The method for producing a micro bubble-containing electrolyte solution according to any one of Supplementary Notes 1 to 5, wherein the filter medium is a membrane filter.

(Supplementary Note 7)

The method for producing a micro bubble-containing electrolyte solution according to any one of Supplementary Notes 1 to 6, wherein the solvent is an aqueous solvent.

(Supplementary Note 8)

The method for producing a micro bubble-containing electrolyte solution according to any one of Supplementary Notes 1 to 7, wherein the solvent is water.

(Supplementary Note 9)

The method for producing a micro bubble-containing electrolyte solution according to any one of Supplementary Notes 1 to 8, wherein the micro bubble contains, as a gas component, at least one selected from the group consisting of hydrogen $(H_2)$, nitrogen monoxide (NO), nitrous oxide $(N_2O)$, carbon monoxide (CO), carbon dioxide $(CO_2)$, nitrogen dioxide $(NO_2)$, hydrogen sulfide $(H_2S)$, oxygen $(O_2)$, ozone $(O_3)$, helium (He), argon (Ar), krypton (Kr), xenon (Xe), nitrogen $(N_2)$, air, methane $(CH_4)$, ethane $(CH_3CH_3)$, propane $(CH_3CH_2CH_3)$, fluoromethane $(CH_3F)$, difluoromethane $(CH_2F_2)$, carbon tetrafluoride $(CF_4)$, and ethylene oxide $(C_2H_4O)$.

(Supplementary Note 10)

The method for producing a micro bubble-containing electrolyte solution according to any one of Supplementary Notes 1 to 9, wherein the electrolyte solution is at least one selected from the group consisting of a physiological saline solution, an extracellular fluid, an intracellular fluid, an infusion, a culture solution, a preservation solution, a perfusate, a dialysate, and a drug solution.

(Supplementary Note 11)

The method for producing a micro bubble-containing electrolyte solution according to any one of Supplementary Notes 1 to 10, including the step of: filling the electrolyte solution into a container.

(Supplementary Note 12)

The method for producing a micro bubble-containing electrolyte solution according to Supplementary Note 11, wherein the container includes a first chamber, a second chamber, and an isolation portion, the first chamber is configured to contain the electrolyte solution, the second chamber is configured to store other component, the isolation portion isolates the first chamber and the second chamber, and allows the first chamber and the second chamber to communicate with each other, and the electrolyte solution is filled into the first chamber in the electrolyte solution-filling.

(Supplementary Note 13)

A method for producing a micro bubble-containing solvent used for preparing a micro bubble-containing electrolyte solution, including the step of:

filtrating a micro bubble-containing solvent with a filter medium, wherein a cation concentration in the micro bubble-containing solvent is less than 20 mmol/l, and the method satisfies at least one of the following conditions (4), (5) and (6):

Condition (4):

a micro bubble density in the micro bubble-containing solvent is $1\times10^6$ bubbles/ml or more;

Condition (5):

the method includes the step of preparing a micro bubble-containing solvent by introducing micro bubbles into a solvent; and Condition (6):

a micro bubble density in the filtrate is $1\times10^5$ bubbles/ml or more.

(Supplementary Note 14)

The method for producing a micro bubble-containing solvent according to Supplementary Note 13, wherein the cation is a monovalent cation.

(Supplementary Note 15)

The method for producing a micro bubble-containing solvent according to Supplementary Note 14, wherein the monovalent cation is at least one of a sodium ion or a potassium ion.

(Supplementary Note 16)

The method for producing a micro bubble-containing solvent according to any one of Supplementary Notes 13 to 15, wherein the filter medium has an absolute pore diameter of 100 to 450 nm.

(Supplementary Note 17)

The method for producing a micro bubble-containing solvent according to any one of Supplementary Notes 13 to 15, wherein the filter medium has an absolute pore diameter of 50 to 220 nm.

(Supplementary Note 18)

The method for producing a micro bubble-containing solvent according to any one of Supplementary Notes 13 to 17, wherein the filter medium is a membrane filter.

(Supplementary Note 19)

The method for producing a micro bubble-containing solvent according to any one of Supplementary Notes 13 to 18, including the step of: filling the micro bubble-containing solvent into a container.

(Supplementary Note 20)

The method for producing a micro bubble-containing solvent according to Supplementary Note 19, wherein:

the container includes a first chamber, a second chamber, and an isolation portion, the first chamber is configured to contain the micro bubble-containing solvent, the second chamber is configured to store other component, the isolation portion isolates the first chamber and the second chamber, and allows the first chamber and the second chamber to communicate with each other, and the micro bubble-containing solvent is filled into the first chamber in the micro bubble-containing solvent-filling.

(Supplementary Note 21)

The method for producing a micro bubble-containing solvent according to Supplementary Note 20, wherein the other component includes an electrolyte.

(Supplementary Note 22)

The method for producing a micro bubble-containing solvent according to any one of Supplementary Notes 13 to 21, wherein the electrolyte solution is at least one selected from the group consisting of a physiological saline solution, an extracellular fluid, an intracellular fluid, an infusion, a culture solution, a preservation solution, a perfusate, a dialysate, and a drug solution.

(Supplementary Note 23)

A method for producing a micro bubble-containing solvent used for preparing a micro bubble-containing electrolyte solution, including the steps of:

adjusting a cation concentration in the micro bubble-containing solvent to less than 20 mmol/l; and filtering a solvent after the adjustment with a filter medium.

(Supplementary Note 24)

The method for producing a micro bubble-containing solvent according to Supplementary Note 21, wherein the method satisfies at least one of the following conditions (4), (5) and (6):

Condition (4):

a micro bubble density in the micro bubble-containing solvent is $1\times10^6$ bubbles/ml or more;

Condition (5):

the method includes the step of preparing a micro bubble-containing solvent by introducing micro bubbles into a solvent; and Condition (6):

a micro bubble density in the filtrate is $1\times10^5$ bubbles/ml or more.

(Supplementary Note 25)

The method for producing a micro bubble-containing solvent according to Supplementary Note 23 or 24, wherein the cation includes a monovalent cation.

(Supplementary Note 26)

The method for producing a micro bubble-containing solvent according to Supplementary Note 25, wherein the monovalent cation is at least one of a sodium ion or a potassium ion.

(Supplementary Note 27)

The method for producing a micro bubble-containing solvent according to any one of Supplementary Notes 23 to 26, wherein the filter medium has an absolute pore diameter of 100 to 450 nm.

(Supplementary Note 28)

The method for producing a micro bubble-containing solvent according to any one of Supplementary Notes 23 to 26, wherein the filter medium has an absolute pore diameter of 50 to 220 nm.

(Supplementary Note 29)

The method for producing a micro bubble-containing solvent according to any one of Supplementary Notes 23 to 28, wherein the filter medium is a membrane filter.

(Supplementary Note 30)

The method for producing a micro bubble-containing solvent according to any one of Supplementary Notes 23 to 29, wherein the solvent is an aqueous solvent.

(Supplementary Note 31)

The method for producing a micro bubble-containing solvent according to any one of Supplementary Notes 23 to 30, wherein the solvent is water.

(Supplementary Note 32)

The method for producing a micro bubble-containing solvent according to any one of Supplementary Notes 23 to 31, wherein the micro bubble contains, as a gas component, at least one selected from the group consisting of hydrogen ($H_2$), nitrogen monoxide (NO), nitrous oxide ($N_2O$), carbon monoxide (CO), carbon dioxide ($CO_2$), nitrogen dioxide ($NO_2$), hydrogen sulfide ($H_2S$), oxygen ($O_2$), ozone ($O_3$), helium (He), argon (Ar), krypton (Kr), xenon (Xe), nitrogen ($N_2$), air, methane ($CH_4$), ethane ($CH_3CH_3$), propane ($CH_3CH_2CH_3$), fluoromethane ($CH_3F$), difluoromethane ($CH_2F_2$), carbon tetrafluoride ($CF_4$), and ethylene oxide ($C_2H_4O$).

INDUSTRIAL APPLICABILITY

As described above, according to the present invention, since a decrease in micro bubbles during filtration can be suppressed, a decrease in micro bubble density in the obtained filtrate can be suppressed as compared with a case where the micro bubble-containing electrolyte solution is filtered. Accordingly, according to the present invention, it is possible to produce an electrolyte solution which can contain a high concentration of micro bubbles. For this reason, the present invention is extremely useful, for example, in the medical field, the pharmaceutical field, and the like.

REFERENCE SIGNS LIST

1: first chamber
10: container
11: electrolyte solution
12: upper end portion
13, 14: sheet
2: second chamber
21: other component
22: discharge portion
3: isolation portion
5: hanging portion 60: production apparatus
61: motor
62a, 62b: tube
63a, 63b: venturi tube
64 a, 64b, 64c connecting tube
65: three-way stopcock

The invention claimed is:

1. A method for producing a micro bubble-containing electrolyte solution, the method comprising:

filtrating a micro bubble-containing solvent with a filter medium to obtain a filtrate; and preparing an electrolyte solution from the filtrate, wherein a cation concentration in the micro bubble-containing solvent is 2 mmol/l or less, wherein the microbubble-containing solvent does not include any monovalent cation; and wherein the method satisfies at least one of the following conditions (1), (2) and (3):

Condition (1):

a micro bubble density in the micro bubble-containing solvent is $1 \times 10^6$ bubbles/ml or more;

Condition (2):

the method comprises the step of preparing the micro bubble-containing solvent by introducing micro bubbles into a solvent; and Condition (3):

a micro bubble density in the electrolyte solution is $1 \times 10^5$ bubbles/ml or more.

2. The method for producing a micro bubble-containing electrolyte solution according to claim 1, wherein the cation is a monovalent cation.

3. The method for producing a micro bubble-containing electrolyte solution according to claim 2, wherein the monovalent cation is at least one of a sodium ion or a potassium ion.

4. The method for producing a micro bubble-containing electrolyte solution according to claim 1, wherein the filter medium has an absolute pore diameter of 100 to 450 nm.

5. The method for producing a micro bubble-containing electrolyte solution according to claim 1, wherein the filter medium is a membrane filter.

6. The method for producing a micro bubble-containing electrolyte solution according to claim 1, wherein the solvent is an aqueous solvent.

7. The method for producing a micro bubble-containing electrolyte solution according to claim 1, wherein the solvent is water.

8. The method for producing a micro bubble-containing electrolyte solution according to claim 1, wherein the micro bubble contains, as a gas component, at least one selected from the group consisting of hydrogen ($H_2$), nitrogen monoxide (NO), nitrous oxide ($N_2O$), carbon monoxide (CO), carbon dioxide ($CO_2$), nitrogen dioxide ($NO_2$), hydrogen sulfide ($H_2S$), oxygen ($O_2$), ozone ($O_3$), helium (He), argon (Ar), krypton (Kr), xenon (Xe), nitrogen ($N_2$), air, methane ($CH_4$), ethane ($CH_3CH_3$), propane ($CH_3CH_2CH_3$), fluoromethane ($CH_3F$), difluoromethane ($CH_2F_2$), carbon tetrafluoride ($CF_4$), and ethylene oxide ($C_2H_4O$).

9. The method for producing a micro bubble-containing electrolyte solution according to claim 1, wherein the electrolyte solution is at least one selected from the group consisting of a physiological saline solution, an extracellular fluid, an intracellular fluid, an infusion, a culture solution, a preservation solution, a perfusate, a dialysate, and a drug solution.

10. The method for producing a micro bubble-containing electrolyte solution according to claim 1, the method comprising:

filling the electrolyte solution into a container.

11. The method for producing a micro bubble-containing electrolyte solution according to claim 10, wherein the container comprises a first chamber, a second chamber, and an isolation portion, the first chamber is configured to contain the electrolyte solution, the second chamber is configured to store other component, the isolation portion isolates the first chamber and the second chamber, and allows the first chamber and the second chamber to communicate with each other, and the electrolyte solution is filled into the first chamber in the electrolyte solution-filling.

12. A method for producing a micro bubble-containing solvent used for preparing a micro bubble-containing electrolyte solution, the method comprising:

filtrating a micro bubble-containing solvent with a filter medium to generate a filtrate, and preparing an electrolyte solution from the filtrate, wherein a cation concentration in the micro bubble-containing solvent is 2 mmol/l or less, wherein the microbubble-containing solvent does not include at least one of monovalent cation and divalent cation; and wherein the method satisfies at least one of the following conditions (4), (5) and (6):

Condition (4):

a micro bubble density in the micro bubble-containing solvent is $1 \times 10^6$ bubbles/ml or more;

Condition (5):

the method comprises the step of preparing a-micro bubble-containing solvent by introducing micro bubbles into a solvent; and Condition (6):

a micro bubble density in a filtrate is $1 \times 10^5$ bubbles/ml or more.

13. The method for producing a micro bubble-containing solvent according to claim 12, wherein the cation is a monovalent cation.

14. The method for producing a micro bubble-containing solvent according to claim 13, wherein the monovalent cation is at least one of a sodium ion or a potassium ion.

15. The method for producing a micro bubble-containing solvent according to claim 12, wherein the filter medium has an absolute pore diameter of 100 to 450 nm.

16. The method for producing a micro bubble-containing solvent according to claim 12, wherein the filter medium is a membrane filter.

17. The method for producing a micro bubble-containing solvent according to claim 12, comprising the step of:

filling the micro bubble-containing solvent into a container.

18. The method for producing a micro bubble-containing solvent according to claim 17, wherein the container comprises a first chamber, a second chamber, and an isolation portion, the first chamber is configured to contain the micro bubble-containing solvent, the second chamber is configured to store other component, the isolation portion isolates the first chamber and the second chamber, and allows the first chamber and the second chamber to communicate with each other, and the micro bubble-containing solvent is filled into the first chamber in the micro bubble-containing solvent-filling.

19. The method for producing a micro bubble-containing solvent according to claim 18, wherein the other component includes an electrolyte.

20. The method for producing a micro bubble-containing solvent according to claim 12, wherein the electrolyte solution is at least one selected from the group consisting of a physiological saline solution, an extracellular fluid, an intracellular fluid, an infusion, a culture solution, a preservation solution, a perfusate, a dialysate, and a drug solution.

21. A method for producing a micro bubble-containing electrolyte solution, the method comprising:

filtrating a micro bubble-containing solvent with a filter medium to obtain a filtrate; and preparing an electrolyte solution from the filtrate, wherein a cation concentration in the micro bubble-containing solvent is 2 mmol/l or less, wherein the microbubble-containing solvent does not include any divalent cation; and wherein the method satisfies at least one of the following conditions (1), (2) and (3):

Condition (1):

a micro bubble density in the micro bubble-containing solvent is $1 \times 10^6$ bubbles/ml or more;

Condition (2):

the method comprises the step of preparing the micro bubble-containing solvent by introducing micro bubbles into a solvent; and Condition (3):

a micro bubble density in the electrolyte solution is $1 \times 10^8$ bubbles/ml or more.

* * * * *